United States Patent [19]

Farnham

[11] Patent Number: 4,586,952
[45] Date of Patent: May 6, 1986

[54] HERBICIDAL SULFONAMIDES

[75] Inventor: William B. Farnham, Wilmington, Del.

[73] Assignee: E. I. Du Pont de Nemours and Company, Wilmington, Del.

[21] Appl. No.: 669,024

[22] Filed: Nov. 7, 1984

Related U.S. Application Data

[60] Division of Ser. No. 435,711, Oct. 21, 1982, Pat. No. 4,486,589, which is a continuation-in-part of Ser. No. 259,982, May 12, 1981, abandoned, which is a continuation-in-part of Ser. No. 168,892, Jul. 11, 1980, abandoned.

[51] Int. Cl.$^4$ .................. C07D 491/098; A01N 47/36
[52] U.S. Cl. ......................................... 71/92; 544/278
[58] Field of Search ............................. 544/278; 71/92

[56] References Cited

FOREIGN PATENT DOCUMENTS 833779 11/1983 South Africa .......................... 71/92

Primary Examiner—Robert Gerstl

[57] ABSTRACT o-Haloalkylbenzene sulfonylureas are useful as herbicides.

7 Claims, No Drawings

HERBICIDAL SULFONAMIDES

RELATED APPLICATION

This application is a division of application Ser. No. 435,711, filed Oct. 21, 1982, now U.S. Pat. No. 4,486,589, which is a continuation-in-part of my application Ser. No. 259,982, filed May 12, 1981, now abandoned, which is a continuation-in-part of Ser. No. 168,892, filed July 11, 1980, now abandoned.

BACKGROUND OF THE INVENTION

This invention relates to o-haloalkylbenzene sulfonyl ureas which are useful as herbicides.

Netherlands Pat. No. 121,788, published Sept. 15, 1966, teaches the preparation of compounds of Formula (i), and their use as general or selective herbicides,

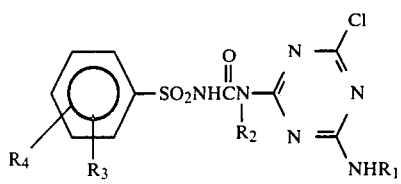

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of Formula (ii), and their use as antidiabetic agents, are reported in J. Drug Res. 6, 123 (1974).

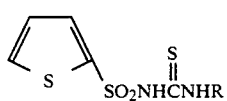

wherein R is pyridyl.

The presence of undesired vegetation causes substantial damage to useful crops, especially agricultural products that satisfy man's basic food needs, such as soybeans, corn, wheat, and the like. The current population explosion and concomitant world food shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need still exists, however, for more effective herbicides that destroy or retard weeds without causing significant damage to useful crops.

In U.S. Pat. No. 4,127,405 compounds of the following formula are taught:

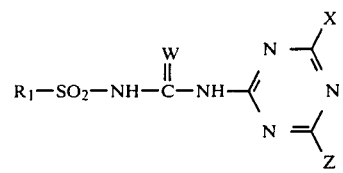

wherein $R_1$ is

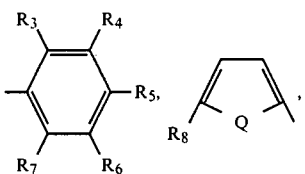

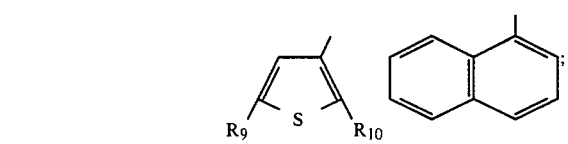

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S-$ or $CH_3OCH_2-$; and Z is methyl or methoxy;

or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ both are hydrogen, at least one of $R_4$, $R_5$ or $R_6$ must be hydrogen.

SUMMARY OF THE INVENTION

This invention relates to novel compounds of Formula I and their agriculturally suitable salts, e.g. Na, K, ammonium, alkyl ammonium, suitable agricultural compositions containing them, and their method of use as pre-emergence and post-emergence herbicides.

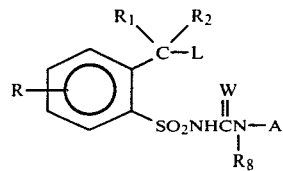

wherein

L is Cl, F, Br, $NR_3R_4$, $N^+R_3R_4R_4'$, $N(R_4)C(O)R_5$, $N(R_4)C(O)NHR_6$ or $N(R_4)C(O)OR_7$;

R is H, F, Cl, Br, $NO_2$, $CF_3$, $C_1-C_3$ alkyl or $C_1-C_3$ alkoxy;

$R_1$ is H, F, Cl or $C_1-C_4$ alkyl;

$R_2$ is H or $CH_3$;

$R_3$ is H, $C_1-C_4$ alkyl or $OCH_3$;

$R_4$ is H or $C_1-C_4$ alkyl;

$R_3$ and $R_4$ can be taken together to form $-(CH_2)_4-$, $-(CH_2)_5-$ or $-(CH_2)_2O(CH_2)_2-$;

$R_4'$ is H, $CH_3$ or $CH_2CH_3$;

$R_5$ is $C_1-C_4$ alkyl optionally substituted with 1-3 atoms of F, Cl or Br, or $C_3-C_4$ alkenyl;

$R_6$ is H, $C_1-C_4$ alkyl or $C_3-C_4$ alkenyl;

$R_7$ is $C_1-C_4$ alkyl;

$R_8$ is H, $CH_3$ or $OCH_3$;

A is

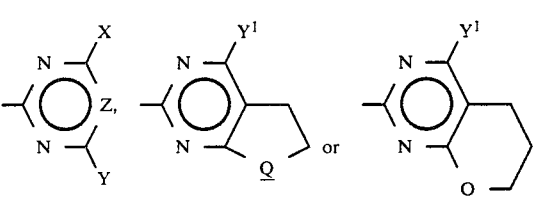

W is O or S;

X is H, Cl, Br, $CH_3$, $CH_2CH_3$, $C_1-C_3$ alkoxy, $CF_3$, $SCH_3$ or $CH_2OCH_3$;

Y is $CH_3$ or $OCH_3$;

Z is N, CH, CCl, CBr, CCN, $CCH_3$, $CCH_2CH_3$, $CCH_2CH_2Cl$ or $CCH_2CH=CH_2$;

$Y^1$ is H, $CH_3$, $OCH_3$ or $OCH_2CH_3$; and

Q is O or $CH_2$;

and their agriculturally suitable salts; provided that:

(1) when $R_1$ is Cl, then L is Cl or Br and $R_2$ is H;

(2) when $R_3$ is $OCH_3$, then $R_4$ is $CH_3$;

(3) when W is S, then $R_8$ is H; and (4) when L is F, then $R_1$ is H, F, or $C_1-C_4$ alkyl.

PREFERRED COMPOUNDS

Preferred in increasing order for their higher activity and/or more favorable ease of synthesis are:

(1) compounds of generic scope wherein Z is N, CH, CCl, CBr or $CCH_3$, W is O, and $R_8$ is H or $CH_3$;

(2) compounds of *preferred* (1) wherein Z is CH or N and X is $CH_3$ of $OCH_3$;

(3) compounds of *preferred* (2) wherein A is

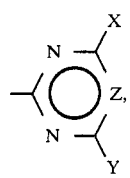

L is Cl, Br or $NR_3R_4$ and $R_8$ is H;

(4) compounds of *preferred* (3) wherein $R_1$ and $R_2$ are H;

(5) compounds of *preferred* (4) wherein R is H; and (6) compounds of *preferred* (5) wherein L is Cl or Br.

Specifically preferred for highest activity and/or most favorable ease of synthesis are:

2-(Dichloromethyl)-N-[(4-methoxy-6-methylpyrimidin-2-yl)aminocarbonyl]benzenesulfonamide;

2-(Dichloromethyl)-N-[(4,6-dimethylpyrimidin-2-yl)aminocarbonyl]benzenesulfonamide;

2-(Dichloromethyl)-N-[(4-methoxy-6-methyl-1,3,5-triazin-2-yl)aminocarbonyl]benzenesulfonamide;

2-(Chloromethyl)-N-[(4,6-dimethoxy-1,3,5-triazin-2-yl)aminocarbonyl]benzenesulfonamide;

2-(Chloromethyl)-N-[(4,6-dimethoxypyrimidin-2-yl)aminocarbonyl]benzenesulfonamide;

2-(Chloromethyl)-N-[(4,6-dimethylpyrimidin-2-yl)aminocarbonyl]benzenesulfonamide;

2-(1-Chloroethyl)-N-[(4,6-dimethoxy-1,3,5-triazin-2-yl)aminocarbonyl]benzenesulfonamide;

2-(1-Pyrrolidinylmethyl)-N-[(4,6-dimethoxypyrimidin-2-yl)aminocarbonyl]benzenesulfonamide, hydrochloride; and 2-(1-Pyrrolidinylmethyl)-N-[(4,6-dimethoxypyrimidin-2-yl)aminocarbonyl]benzenesulfonamide.

This invention also relates to novel compounds of Formula II which are useful intermediates for the preparation of the herbicidal compounds of Formula I.

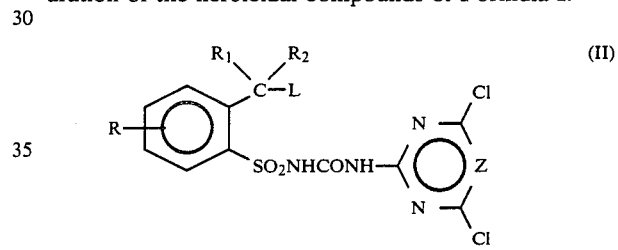

wherein

R, $R_1$, $R_2$ and L are as previously defined; and

Z is CH or N; provided that (1) when $R_1$ is Cl, then L is Cl or Br and $R_2$ is H;

(2) when L is $NR_3R_4$ or $N^+R_3R_4R_4'$, then $R_3$ or $R_4$ can not be H; and (3) when $R_3$ is $OCH_3$, then $R_4$ is $CH_3$.

This invention also relates to novel compounds of Formula IV which are useful intermediates for the preparation of the compounds of Formula I.

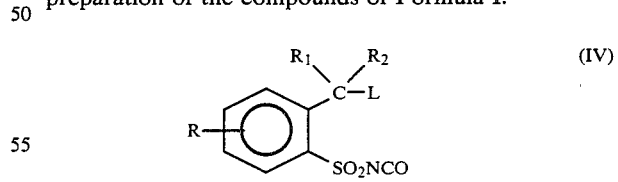

wherein

R, $R_1$ and $R_2$ are as previously defined; and L is Cl, F, Br, $NR_3R_4$ or $N^+R_3R_4R_4'$. provided that (1) when $R_1$ is Cl, then L is Cl or Br and $R_2$ is H;

(2) when L is $NR_3R_4$ or $N^+R_3R_4R_4'$, then $R_3$ and $R_4$ cannot be H; and (3) when $R_3$ is $OCH_3$, then $R_4$ is $CH_3$.

SYNTHESIS

As shown in Equation 1, the compounds of Formula I where W=0, can be prepared by combining an appropriate 2-aminoheterocycle of Formula V with an appropriately substituted sulfonyl isocyanate of Formula IV R, $R_1$, $R_2$, $R_8$, L and A being as previously defined and L is Cl, Br, $NR_3R_4$ and $NR_3R_4R_4'$ where $R_3$, $R_4$ and $R_4'$ are as previously defined provided $R_3$ and $R_4$ cannot be H.

EQUATION 1

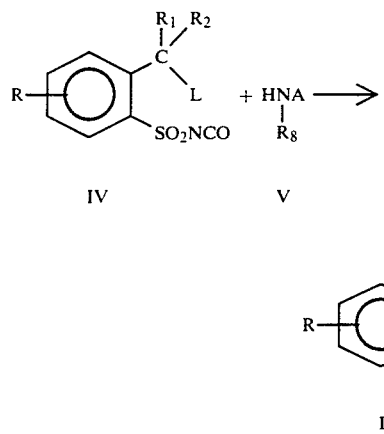

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminoheterocycle. Since isocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

The intermediate sulfonyl isocyanates of Formula IV can be prepared by reacting corresponding sulfonamides with phosgene in the presence of an alkyl isocyanate such as butyl or cyclohexyl isocyanate at reflux in a solvent such as chlorobenzene, according to the procedure of H. Ulrich and A. A. Y. Sayigh, *Newer Methods of Preparative Organic Chemistry*, Vol. VI, p. 223–241, Academic Press, New York and London, W. Foerst, Ed. In cases where formation of the desired sulfonyl isocyanate is difficult by the above procedure, the preformed sulfonylurea from the reaction of butyl isocyanate with the appropriate sulfonamide is contacted with phosgene according to the above reference.

Alternatively, the process of Ulrich and Sayigh can be improved by the addition of a tertiary base to the reaction mixture as shown by Equation 2. R, $R_1$, $R_2$ and L are as previously defined above in Equation 1.

EQUATION 2

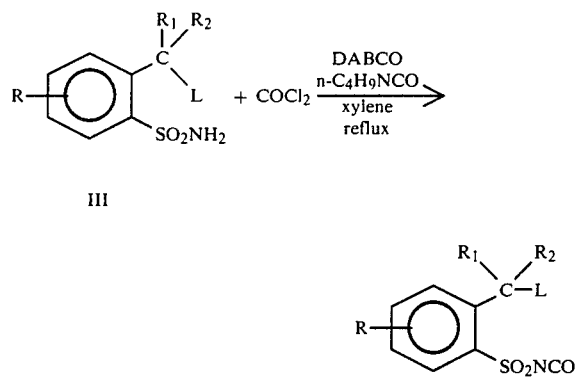

A mixture of the appropriate benzenesulfonamide III, an alkyl isocyanate such as butyl isocyanate and a catalytic amount of 1,4-diaza[2,2,2]bicyclooctane (DABCO) in xylene or other inert solvent of sufficiently high boiling point (e.g. >135°) is heated to approximately 135°. Phosgene is added to the mixture until an excess is present as indicated by a drop in the boiling point. (The mixture is heated further to drive off the excess phosgene.) After the mixture is cooled and filtered to remove a small amount of insoluble by-products, the solvent and alkyl isocyanate are distilled off in vacuo leaving a residue which is the crude sulfonyl isocyanate IV.

The preparation of sulfonamides from ammonium hydroxide and sulfonyl chlorides is widely reported in the literature, e.g. Crossley et al., *J. Am. Chem. Soc.*, 60, 2223 (1938).

For those examples containing reactive functionality in the position ortho to the sulfonamide moiety, it is convenient to add the sulfonyl chloride to a measured quantity of ammonia (Equation 3) in an inert solvent, e.g. tetrahydrofuran, ethyl acetate, etc., at low temperature ($-78°$ to $0°$). Side reactions such as ring formation, elimination, or ciondensation are thereby substantially avoided.

EQUATION 3

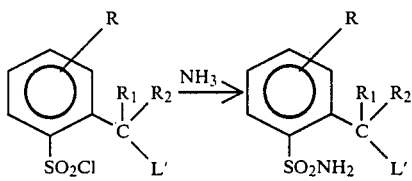

$L' = Cl$, Br
R, $R_1$ and $R_2$ as above.

The α-haloalkylbenzenesulfonamides may be converted to other required intermediates for this invention by treatment with appropriate reagents as described in Equation 4 and Example 18.

EQUATION 4

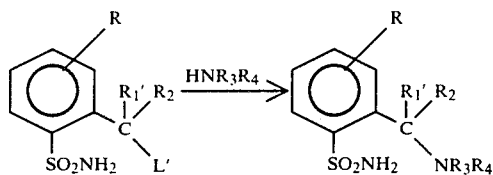

$R_1' = H, C_1-C_4$ alkyl
$L' = Cl, Br$

The various intermediates i serve as precursors to other required compounds of this invention.

Ammonium salts can be prepared by alkylation as described in Equation 5 and Example 19.

EQUATION 5

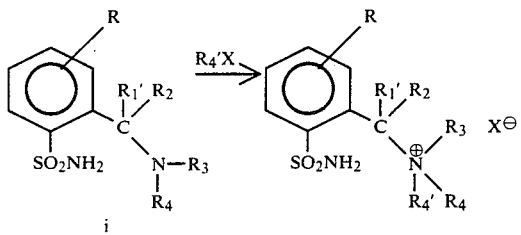

Various amides, ureas and carbamates may be produced by well-known reactions of the primary or secondary amine i (at least one of $R_3$ and $R_4$ is H) with the desired acyl chloride, carbamoyl chloride, or chloroformate (Equation 6):

EQUATION 6 e.g.

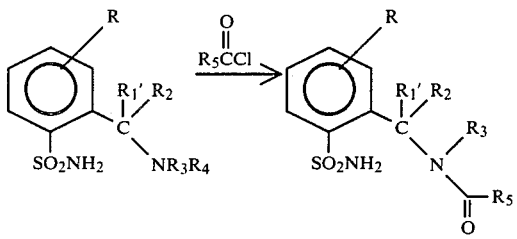

Certain sulfonyl chlorides are best prepared by chlorosulfonation of a substituted benzene according to the teaching of H. T. Clarke et al. Org. Synth., Coll. Vol. 1, 2nd Ed. 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, J. Org. Chem., 25, 1824 (1960).

Substituted benzenesulfonyl chlorides containing an ortho α-haloalkyl group can be made by methods known in the art. α-Chloroalkyl- and dichloromethylbenzenesulfonyl chlorides can be made by contacting the corresponding alkylbenzenesulfonyl chlorides with with dichlorine monoxide in an inert solvent, most conveniently in the temperature range 40°–80°. The degree of chlorination is determined by the relative quantity of dichlorine monoxide employed. (Equation 7). (F. D. Marsh, U.S. Pat. No. 4,226,783 issued Oct. 7, 1980).

EQUATION 7

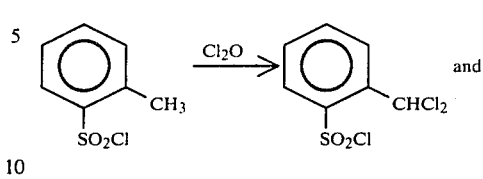 and

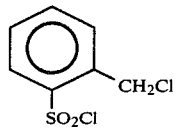

A series of standard functional group transformations may also be used as described (J. F. King, A. Hawson, B. L. Huston, L. J. Danks, and J. Komery, Can. J. Chem., 49, 943 (1971) for 2-(chloromethyl)benzenesulfonyl chloride (Equation 8).

EQUATION 8

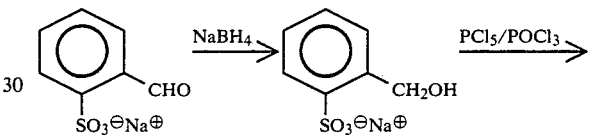

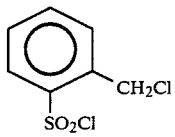

Benzylic bromination using N-bromosuccinimide is useful in the preparation of α-bromoalkylbenzenesulfonyl chlorides (Equation 9).

EQUATION 9

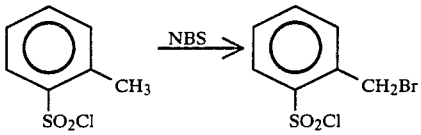

[W. B. Renfrow and M. Devadoss, J. Org. Chem., 40, 1525 (1975)].

α-Fluoroalkyl substituted derivatives can be prepared by substituting fluorine for chlorine. Thus an o-alkylnitrobenzene can be chlorinated (or dichlorinated) by the method of F. D. Marsh (op. cit.). These can be converted to the corresponding fluoro derivatives according to methods such as described in "Aromatic Fluorine Compounds" A. E. Panlath and A. J. Teffler, Reinhold Publ. Co., New York (1962) or W. J. Middleton U.S. Pat. No. 3,940,402, issued Feb. 24, 1976, as shown by Equation 9a wherein R, $R_1$, and $R_2$ are as previously defined.

EQUATION 9a

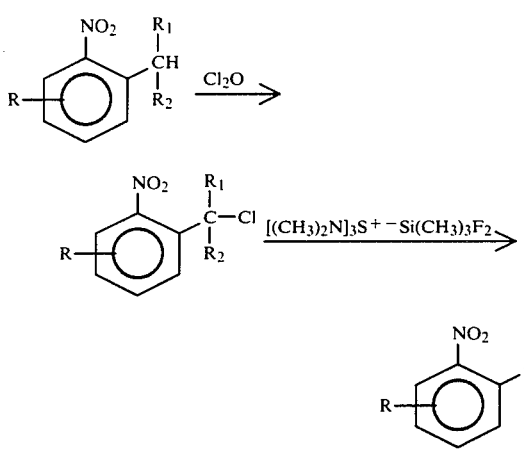

Conversion of the nitrobenzene derivative, obtained according to Equation 9a, to anilines can be carried out by a variety of methods (c.f. Compendium of Organic Synthetic Methods II, page 104, I. T. Harrison and S. Harrison, J. Wiley and Sons, New York, 1974) and these can be converted to the corresponding sulfonyl chlorides by the method of H. L. Yale and F. Sowinski (op. cit).

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines," Vol. XVI of the above series.

2-Amino-1,3,5-triazines can be synthesized according to the methods described by E. M. Smolin and L. Rapaport in "s-Triazines and Derivatives," Vol. XIII of the same series.

The preparation of fused ring pyrimidine amines is disclosed in unexamined European Patent No. 15683.

Compounds of Formula I can also be prepared by the method described in Equation 10 where Z is CH or N and R, $R_1$ and $R_2$ are as previously defined, provided that when L is $NR_3R_4$ or $NR_3R_4R_4$ then $R_3$ or $R_4$ cannot be H.

EQUATION 10

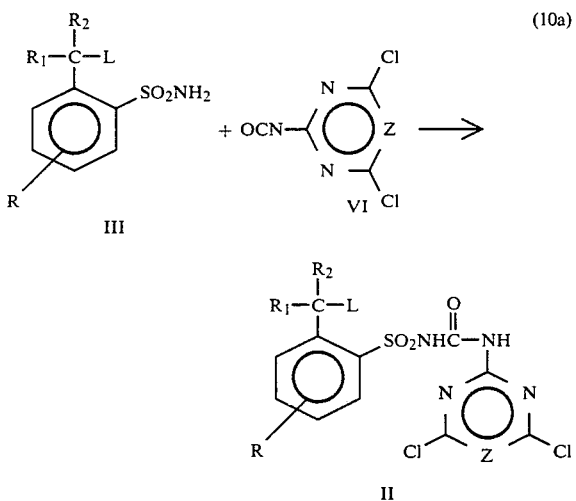

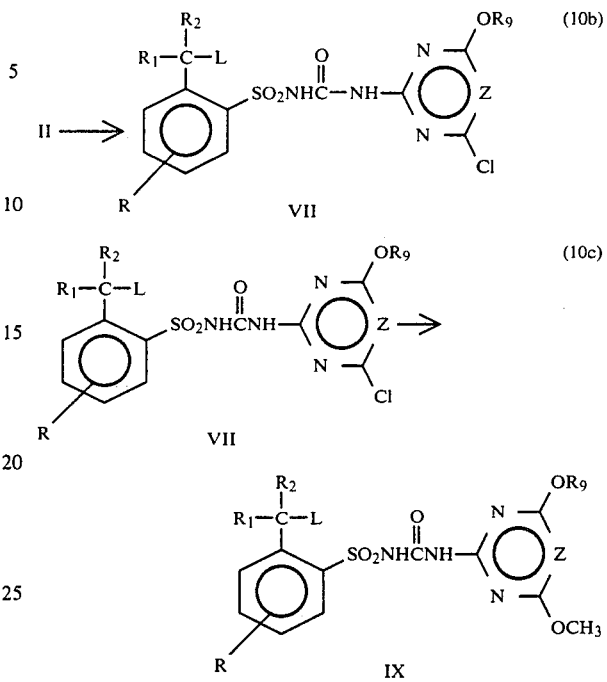

wherein
R, $R_1$ and $R_2$ are as described in Equation 1;
L is as defined for Formula II;
Z is CH or N; and
$R_9$ is $C_1$–$C_3$ alkyl.

REACTION STEP 10a

In Reaction Step 10a an aromatic sulfonamide of Formula III is contracted with a heterocyclic isocyanate of Formula VI to yield an N-(haloheterocyclicaminocarbonyl)aromatic sulfonamide of Formula II.

The heterocyclic isocyanates used in Reaction (10a) may be prepared according to methods described in Swiss Pat. No. 579,062, U.S. Pat. No. 3,919,228, U.S. Pat. No. 3,732,223 and *Angew Chem. Int. Ed.*, 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.-2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

REACTION STEPS 10b and 10c

In Reaction Steps 10b and 10c, one or two of the chlorine atoms on the heterocyclic ring of the compound of Formula II is displaced by a nucleophilic species. Generally, this may be done by contacting the compound of Formula II either with alkanol, $R_9OH$, or with alkoxide, $-OR_9$, where $R_9$ is as described above.

Thus, in Reaction Step (10b), a compound of Formula II can be contacted with at least on equivalent of alkanol, $R_9OH$. This reaction is sluggish, however, and it is preferred to contact the compound of Formula II with at least two equivalents of alkoxide, $-OR_9$. The alkoxide can be provided in a number of ways:

(a) The compound of Formula II can be suspended or dissolved in an alkanol solvent, $R_9OH$, in the presence of at least two equivalents of alkoxide, $-OR_9$. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when $R_9$ is methyl, the compound of Formula II could be suspended or dissolved in methanol in the presence of two equivalents of sodium methoxide.

(b) Alternatively, two equivalents of sodium hydride could be used in place of the sodium methoxide. The compound of Formula II can be suspended or dissolved in an inert solvent in the presence of at least two equivalents of alkoxide, $-OR_9$. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when $R_9$ is methyl, the compound of Formula II could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (b) whereas only one equivalent of alkanol is needed for the same process. This difference is due to the reaction which is believed to occur between the alkoxide and the sulfonyl nitrogen of the sulfonamide of Formula II. When alkoxide is used, the first equivalent of alkoxide removes a proton from the sulfonyl nitrogen, and is only the second equivalent which effects displacement of the halogen. As a result, two equivalents of alkoxide are required. The resulting salt must be acidified, i.e., with sulfuric, hydrochloric or acetic acid, to yield a compound of Formula VII. There is, of course, no intent to be bound by the mechanism described above.

In Reaction Step (10c), a compound of Formula VII substituted with at least one displaceable group, is contacted with either one equivalent of methanol or with two equivalents of methoxide. The compound of Formula VII is prepared according to Reaction Step (10b), from a compound of Formula II. When methoxide is used, it may be provided in either of the methods described above in connection with Reaction Step (10b) and the resulting salt can be acidified to yield a compound of Formula IX.

When $R_9=CH_3$, Reaction Steps (10b) and (10c) may be combined. Thus, a compound of Formula II may be contacted either with at least two equivalents of methanol or with at least three equivalents of methoxide.

For a compound of Formula II, certain reaction conditions will favor displacement of only one of the chlorine groups. These conditions are the use of low temperatures and, when alkoxide is used, the slow addition of the stoichiometric amount of alkoxide or alkoxide-generating base to the medium containing the compound of Formula VII.

When alkoxide is used, both Reaction Steps (10b) and (10c) are preferably run at temperatures within the range of about $-10°$ C. to 80° C., the range of about 0° to 25° C. being more preferred. Reaction Steps (10b) and (10c) are more sluggish when alkanol is used instead of alkoxide, and more drastic conditions are required for the reaction to go to completion. Thus, higher temperatures, up to and including the boiling point of the alkanol itself, are required.

As shown in Equation 11, compounds of Formula I, wherein A, R, $R_1$ and $R_2$ are as previously defined, provided that when L is $NR_3R_4$ or $NR_3R_4R_4'$ then $R_3$ or $R_4$ cannot be H, are prepared by the reaction of an appropriately substituted sulfonamide (III) with the appropriate heterocyclic isothiocyanate of Formula X.

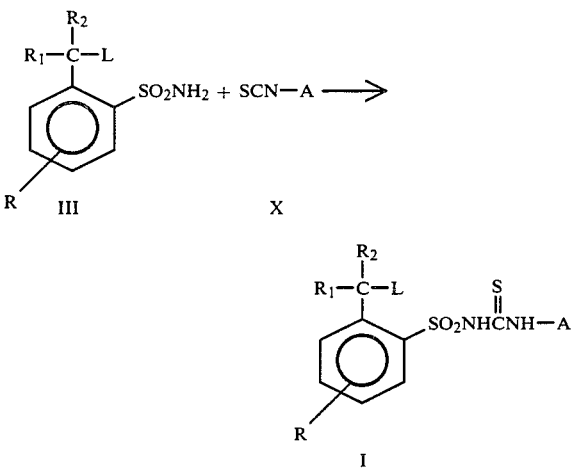

The reaction of Equation 11 is best carried out by dissolving or suspending the sulfonamide and isothiocycante in a polar solvent such as acetone, acetonitrile, ethyl acetate or methylethylketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute minteral acid and filtering off the insoluble product.

The heterocyclic isothiocyanates which are used in the procedure of Equation 11 are prepared, for example, according to the method of Japan patent Application Pub: Kokai No. 51-143686, June 5, 1976, or that of W. Abraham and G. Barnikow Tetrahedron 29, 691–7 (1973).

The disclosures of all references cited above are herein incorporated by reference.

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like. One such addition salt is described in Examples 8 and 9.

The 2-(1-haloalkyl)benzenesulfonyl ureas are also useful precursors to other herbicidal sulfonyl ureas of this invention:

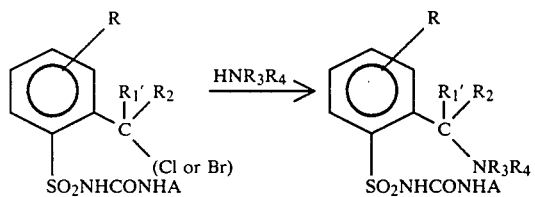

R, $R_2$, A are as above with the proviso that X,Y,Y'≠Cl,Br, $R_1'$=H, $C_1$-$C_4$ alkyl The above reaction is conveniently carried out in a solvent such as dimethylformamide or acetonitrile. Details are provided in Examples 8 and 9.

EXAMPLE 1

2-(Dichloromethyl)-N-[(4-methoxy-6-methylpyrimidin-2-yl)aminocarbonyl]benzenesulfonamide

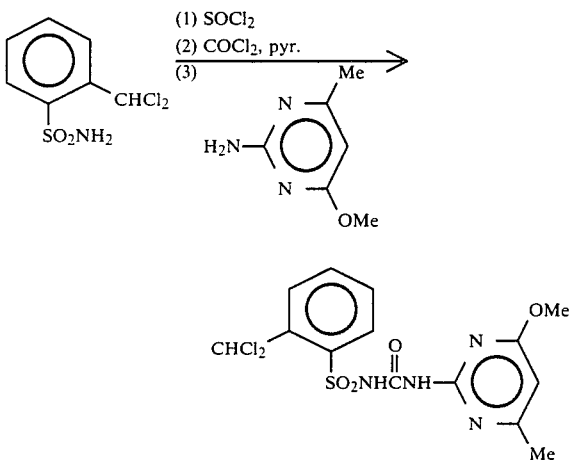

o-Dichloromethylbenzenesulfonamido (2.40 g, 10 mmol) was treated with thionyl chloride (25 ml) and heated to reflux for 16 hrs. Volatiles were removed under vacuum and the residue was treated with thionyl chloride (20 ml) and refluxed for 22 hrs. Thionyl chloride was removed under vacuum, and two portions of dry toluene were added and evaporated in order to remove last traces of $SOCl_2$. The crude product in toluene (45 ml) was transferred to a threeneck flask, treated with dry pyridine (1.0 ml), and then treated slowly with phosgene such that a slow reflux was maintained while the internal temperature was held at ca. 70° for 1.0 hr. Excess phosgene was removed using a stream of dry nitrogen. IR of the crude residue showed only a trace NH stretch and featured a strong band at 2250 $cm^{-1}$.

The crude isocyanate in dry acetonitrile (15 ml) was treated with 2-amino-4-methoxy-6-methyl pyrimidine (1.39 g, 10 mmol). The amine dissolved and a precipitate formed. The mixture was stirred for 16 hrs, filtered, and the solid was washed with ca. 3 ml acetonitrile to give 1.51 g of off-white solid, mp 183°-185° C.

$^1$H nmr: $\delta_{DMSO-d_6}^{TMS}$ 10.3 (brd s, NH), 8.25-7.58 (m, featuring singlet at 8.13), 6.62 (s) 3.98 (s), 2.42 (s).

Recrystallization from $CHCl_3$ gave 0.89 g, mp 189°-190° (dec.).

Mass spec: measured 404.0083; calc'd for $C_{14}H_{14}N_4O_4SCl_2$ 404.0110.

Anal. Calc'd: C, 41.49; H, 3.48; N, 13.83. Found: C, 41.22; H, 3.21; N, 13.83; C, 41.12; H, 3.50; N, 13.67.

EXAMPLE 2

2-(Dichloromethyl)-N-[(4,6-dimethylpyrimidin-2-yl)aminocarbonyl]benzenesulfonamide

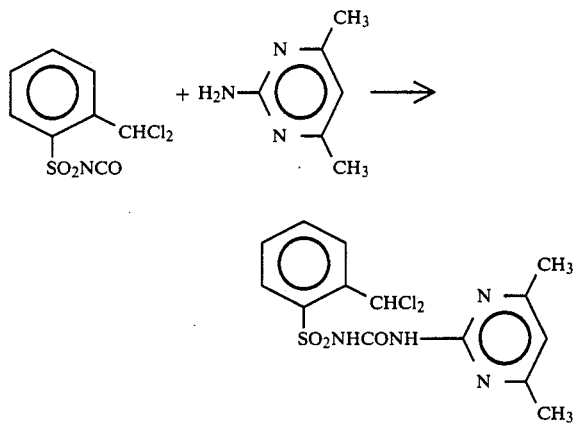

2-(Dichloromethyl)benzenesulfonyl isocyanate, prepared from 10 mmol of sulfonamide as described in the synthesis of Example 1, was treated with acetonitrile and 2-amino-4,6-dimethylpyrimidine (1.23 g). The mixture was stirred at room temperature for 18 hrs, cooled, and filtered to provide 1.08 g of white solid, mp 195°-197° (Dec).

$^1$H nmr $\delta_{CDCl_3/DMSO-d_6}^{TMS}$ 10.53 (s), 8.20-7.90 (m, featuring singlet at 8.00), 7.87-7.43 (m), 6.83 (s), 2.43 (s).

IR (nujol) featured bands at 1710 and 1600 $cm^{-1}$.

Mass spectrum featured m/e 388.0174 (calc'd for $C_{14}H_{14}Cl_2N_4O_3S$ 388.0163); 150.0627 (calc'd for $C_7H_7N_3$ 150.0667).

EXAMPLE 3

2-(Dichloromethyl)-N-[(4-methoxy-6-methyl-1,3,5-triazin-2-yl)aminocarbonyl]benzenesulfonamide

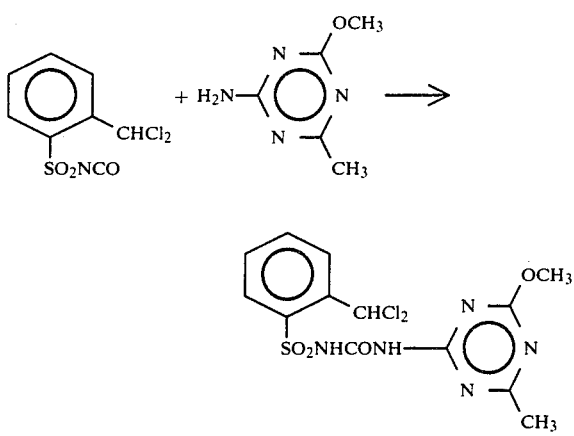

2-(Dichloromethyl)benzenesulfonyl isocyanate prepared from 10 mmol of sulfonamide as described in the synthesis of Example 1, was treated with acetonitrile (15 ml) and 2-amino-4-methoxy-6-methyl-1,3,5-triazine (1.40 g). The mixture was stirred for 18 hrs. and filtered. The filtrate was evaporated and recrystallized from acetone to give 0.78 g of white solid, mp 168°–169° (dec).

$^1$H nmr $\delta_{DMSO\text{-}d_6}^{TMS}$ 8.37–7.50 (m, featuring singlet at 8.07), 7.00–6.17 (brds), 4.00 (s), 2.48 (s).

IR (nujol) featured bands at 1720 and 1590 cm$^{-1}$.

Mass spectrum featured 264.9367 (calc'd for $C_8H_5Cl_2NO_3S$ 264.9367) and 140.0687 (calc'd for $C_5H_8N_4O$ 140.0697).

Anal. Calc'd:C, 38.44; H, 3.23; N, 17.24; Found: C, 38.74; H, 3.13; N, 16.90; C, 38.59; H, 3.11; N, 17.04.

EXAMPLE 4

2-(Chloromethyl)-N-[(4,6-dimethoxy-1,3,5-triazin-2-yl)aminocarbonyl]benzenesulfonamide

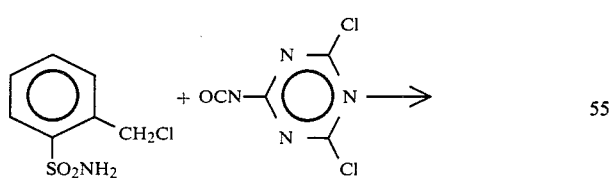

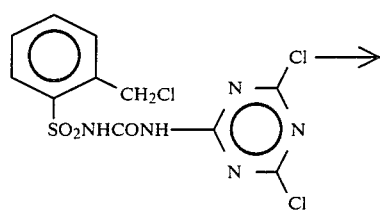

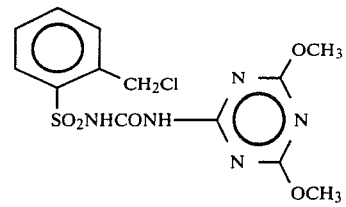

A solution of 4,6-dichloro-1,3,5-triazin-2-yl isocyanate (3.10 g, 16.2 mmol) in acetonitrile (15 ml) was contacted with 2-(chloromethyl)benzene sulfonamide (3.34 g, 16.2 mmol) and stirred for 20 hrs at 25°. The mixture was heated at 50° for 2 hrs, cooled and filtered to provide 3.86 g, mp 162°–170°, which was contacted with sodium methoxide (30 mmol) in methanol (60 ml) at 20°–25° for 16 hrs. Water (100 ml) was added and the mixture was filtered and neutralized by addition of hydrochloric acid. Filtration and drying gave 2.20 g of white solid, mp 150°–152° (dec.).

$^1$H nmr $\delta_{DMSO\text{-}d_6}^{TMS}$ 11.0 (s), 8.30–7.50 (m), 5.23 (s), 4.03 (s).

IR (nujol) featured absorption bands centered at 3200, 1720, 1610 and 1560 cm$^{-1}$.

Anal. Calc'd for $C_{13}H_{14}N_5ClO_4S$ C, 40.26; H, 3.64; N, 18.06. Found C, 38.60; H, 3.62; N, 18.40.

EXAMPLE 5

2-(Chloromethyl)-N-[(4,6-dimethoxypyrimidin-2-yl)aminocarbonyl]benzenesulfonamide

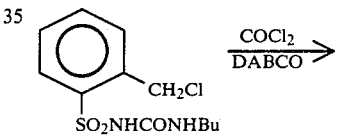

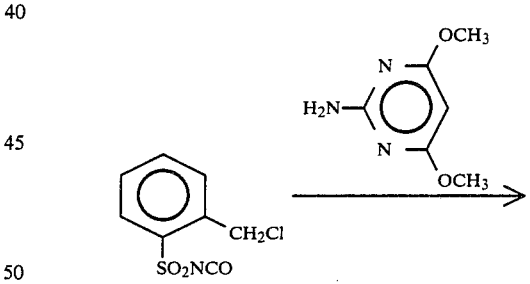

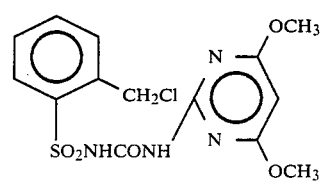

A solution of 2-(chloromethyl)-N-(butylaminocarbonyl)benzene sulfonamide (1.33 g, 4.38 mmol) and diazabicyclo[2.2.2]octane (5 mg) in xylene (12 ml) was heated at reflux and contacted in portions with phosgene (1.0 ml. condensed phase). After 2.0 hrs at reflux, the mixture was cooled to room temperature, decanted, and volatiles were removed to give 1.56 g of crude product. The IR spectrum of 2-(chloromethyl)benzenesulfonyl isocyanate featured a strong band at 2250 cm$^{-1}$. The crude sulfonyl isocyanate was contacted with acetonitrile (10 ml) and 2-amino-4,6-dimethoxypyrimidine (0.68 g, 4.4 mmol) and stirred for 16 hrs. Filtration gave 1.18 g of white solid, mp 192°–193°. The sample was dissolved in 0.5N NaOH, filtered and pH adjusted to 6.5. The mixture was cooled and filtered and the solid washed with ice water and dried to give 0.90 g of white solid.

$^1$H nmr $\delta_{DMSO\text{-}d_6}^{TMS}$ 12.7 (brd s, 10.50 (s, 1H) 8.13–7.97 (m, 1H), 7.73–7.40 (m, 3H), 5.90 (s, 1H), 5.10 (s, 2H), 3.87 (s, 6H).

Anal. Calc'd: C, 43.47; H, 3.91; N, 14.48; S, 8.29. Found: C, 41.76; H, 3.82; N, 13.94; S, 8.23.

EXAMPLE 6

2-(Chloromethyl)-N-[(4,6-dimethylpyrimidin-2-yl)aminocarbonyl]benzenesulfonamide

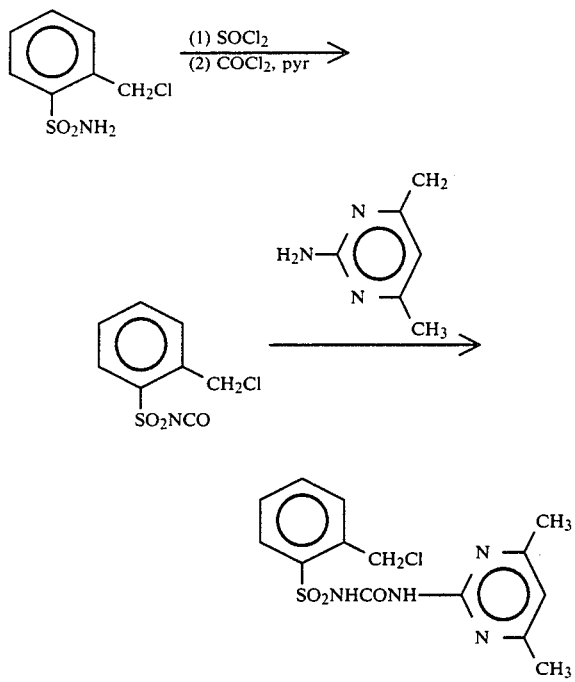

A mixture of 2-(chloromethyl)benzene sulfonamide (4.11 g, 20 mmol) and thionyl chloride (35 ml) was heated to reflux for 36 hrs. Thionyl chloride was removed under vacuum. The residue was contacted with toluene (100 ml) and pyridine (2 ml), heated to 70°, and treated in portions with phosgene (excess) for 2.0 hrs. The mixture was cooled, and the toluene-soluble portion was decanted and evaporated to give a residue which was treated with acetonitrile (15 ml) and 2-amino-4,6-dimethylpyrimidine (1.70 g, 13.8 mmol). After 16 hrs, the solid was filtered and washed with acetonitrile to give 1.45 g of solid which was taken up in 1.0N NaOH and filtered. The pH was adjusted to 6.0 with dilute hydrochloric acid and the solid was filtered and dried to provide 1.34 g of creamcolored solid, mp 176°–177° (dec.)

IR (KBr) featured absorption bands at 3340–2300,1700 (strong), 1600, 1500, 1440, 1340 cm$^{-1}$.

EXAMPLE 7

2-(1-Chloroethyl)-N-[(4,6-dimethoxy-1,3,5-triazin-2-yl)aminocarbonyl]benzenesulfonamide

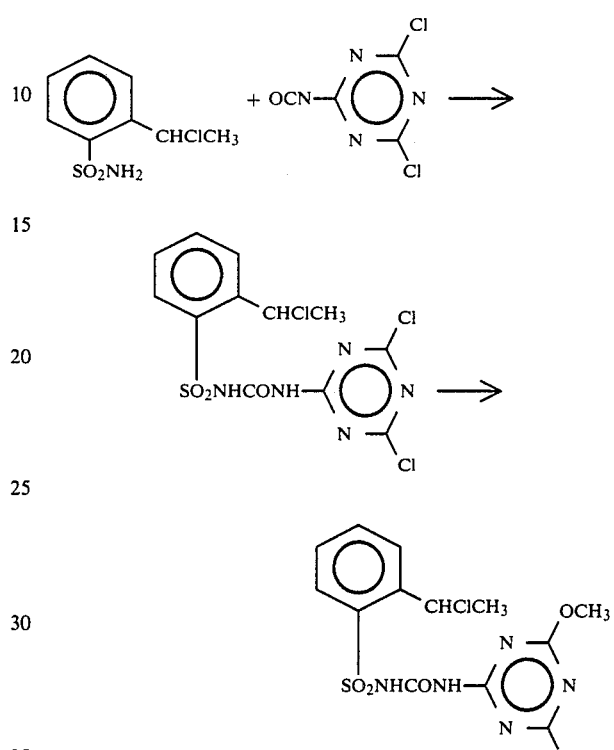

A solution of 4,6-dichloro-1,3,5-triazin-2-yl isocyanate (2.27 g, 11.9 mmol) in acetonitrile (20 ml) was contacted with 2-(1-chloroethyl)benzenesulfonamide (2.61 g, 11.9 mmol) and stirred at 25° for 18 hrs. and at 50° for 2.0 hrs. Solvent was evaporated to give 4.95 g of residue.

$^1$H nmr $\delta_{CDCl_3}^{TMS}$ 11.35 (s), 8.87 (s), 8.33–7.30 (m), 6.18 (q, J=7 Hz), 5.50 (s), 1.88 (d, J=7 Hz).

Mass Spectrum: observed 244.9915 (calc'd for C$_9$H$_8$O$_3$NClS 244.9913), 163.9643 (calc'd for C$_3$H$_2$N$_4$Cl$_2$ 163.9656).

A solution of the above sulfonyl urea in methanol (20 ml) was contacted with a solution of sodium methoxide (36 mmol) in methanol (65 ml) at 0° for 3.0 hrs. Solvent was evaporated and the residue was taken up in water (120 ml), filtered, and pH was brought to 5.0 g with dilute HCl. The mixture was cooled and filtered and the solid was washed with the water and dried to give 3.52 g of white solid, mp 148°–150° (dec.).

$^1$H nmr $\delta_{(CD_3)_2CO}^{TMS}$ 8.30–7.42 (M), 6.32 (q, J=7 Hz), 4.08 (s), 2.93 (brds), 1.88 (d, J=7 Hz).

Mass spectrum showed: 244.9912 (calc'd for C$_9$H$_8$O$_3$NClS 244.9913) 156.0616 (calc'd for C$_5$H$_8$O$_2$N$_4$ 156.0647)

Anal. Calc'd: C, 41.85; H, 4.01; N, 17.43. Found: C, 41.92; H, 4.05; N, 17.02.

EXAMPLE 8

2-(1-Pyrrolidinylmethyl)-N-[(4,6-dimethoxypyrimidin-2-yl)aminocarbonyl]benzenesulfonamide, hydrochloride salt

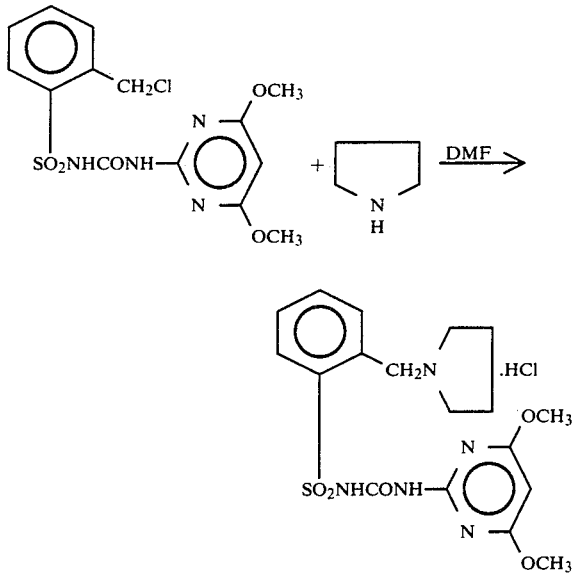

A slurry of 2-(chloromethyl)-N-[(4,6-dimethoxypyrimidin-2-yl)aminocarbonyl]benzenesulfonamide (1.00 g) in dimethylformamide (5 ml) was contacted with pyrrolidine (0.45 ml) and stirred for 3.5 hrs. Volatiles were removed under vacuum and the residue was taken up in methanol. Solvent was removed and the water (15 ml) was added and the pH was adjusted to 6.0 by addition of dilute hydrochloric acid. Cooling and scratching produced a white solid which was collected and dried to give 488 mg, m.p. 117°–123°. A 400 mg sample was crystallized from acetonitrile to give 269 mg. m.p. 132°–134° C.

$^1$H nmr $\delta_{CDCl_3}^{TMS}$ 13.0–11.0 (brds 2H), 8.63 (s, 1 NH), 8.37–8.20, 8.05–7.90, and 7.70–7.33 (m, 4H), 5.68 (s, 1H), 5.00 (s, 2H), 3.90 (s, 6H), 3.70–2.90 (m, 4H), 2.30–1.90 (m, 4H).

IR (KBr) 3650–2200, 1710, 1610, 1580, 1450, 1360, 1200, 1165 are major absorption bands.

Anal. Found C, 44.99; H, 5.17; N, 14.56. Calc'd for C$_{18}$H$_{23}$N$_5$O$_5$S·HCl C, 47.21; H, 5.28; N, 15.30.

EXAMPLE 9

2-(1-Pyrrolidinylmethyl)-N-[(4,6-dimethoxypyrimidin-2-yl)aminocarbonyl]benzenesulfonamide

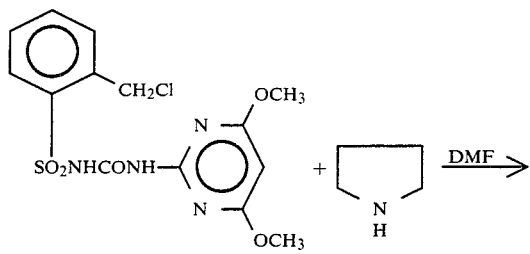

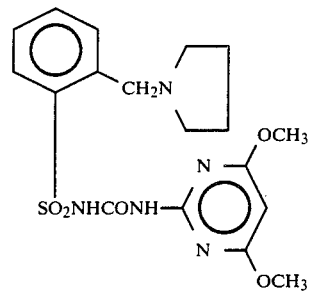

A slurry of 2-(chloromethyl)-N-[(4,6-dimethoxypyrimidin-2-yl)aminocarbonyl]benzenesulfonamide (1.00 g) in dimethylformamde (5 ml) was contacted with pyrrolidine (0.45 ml) and stirred for 2.5 hrs. Volatiles were removed under vacuum and the residue was washed several times with ether, taken up in methanol and treated dropwise with a ca.0.5% solution of dry hydrochloric acid in methanol to adjust the apparent pH to 6.5–7.0. Volatiles were again removed to provide 1.34 g. of glassy foam which was chromatographed on silica gel eluting with 2/1 ethyl acetate/methanol. Residues from the major fractions were taken up in warm chloroform and evaporated. Addition of a small volume of acetonitrile yielded, upon cooling and scratching, a total of 280 mg of white solid, up 138°–140° (dec).

$^1$H nmr $\delta_{CDCl_3}^{TMS}$ 8.10–7.90 (m, 1H), 7.67–7.10 (m, 4H, featuring NH singlet at 7.57), 5.50 (s, 1H), 4.60 (s, 2H), 3.72 (s, 6H), 3.43–3.10 (m, 4H), 2.30–1.90 (m, 4H).

IR (KBr) 3680–2300, 1660, 1600, 1450, 1370, 1280, 1150, and 1110 cm$^{-1}$ were major absorption bands.

Anal. Calc'd for C$_{18}$H$_{23}$N$_5$O$_5$S C, 51.29; H, 5.50; N, 16.62. Found: C, 50.40; H, 5.29; N, 15.86.

Contacting a CDCl$_3$ solution of the above compound with dry hydrochloric acid produced the same substance described in Example 8 as judged by $^1$H nmr and IR spectral data.

EXAMPLE 10

2-(1-Chloroethyl)benzenesulfonyl chloride

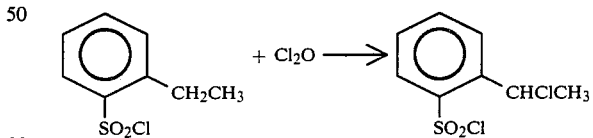

A solution of 2-ethylbenzenesulfonyl chloride (obtained by chlorosulfonation of ethylbenzene) (7.78 g) in carbon tetrachloride (5.0 ml) was contacted with a solution of dichlorine monoxide (82 mmol) in carbon tetrachloride (100 ml) and the mixture was heated in a closed system at 50°–60° for 16 hrs. The mixture was dried (MgSO$_4$) and volatiles were removed under vacuum. The residue was kugelrohr distilled to give 7.63 g of colorless oil, bp 75°–80° (0.15 mm).

$^1$H nmr $\delta_{CDCl_3}^{TMS}$ 8.20–7.35 (m). 6.13 (q, J=7 Hz), 1.90 (d, J=7 Hz).

EXAMPLE 11

2-Dichloromethylbenzene sulfonamide

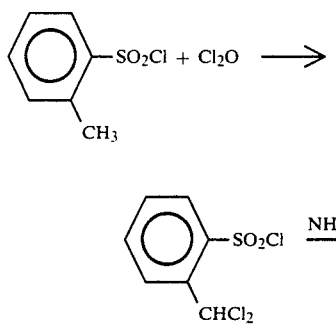

A solution of o-methylbenzenesulfonyl chloride (7.97 g, 42 mmol) in CCl$_4$ (10 ml) was contacted with a solution of Cl$_2$O in CCl$_4$ (108 ml, 96 mmol) and the mixture was heated at 50° for 23 hrs. The cooled solution was purged with a stream of nitrogen, dried (MgSO$_4$), and evaporated to give 10.1 g of white solid. $^1$H nmr: 8.43–7.47 (m, featuring a singlet at 7.82).

The product sulfonyl chloride was dissolved in tetrahydrofuran (50 ml) and was added to a solution of ammonia (2.7 ml at −78°) in tetrahydrofuran (100 ml) at −78°. The mixture was allowed to warm slowly to 5°. Solvent was removed under vacuum, and the residue was taken up in CH$_2$Cl$_2$, washed with water, dried, and evaporated to give 8.3 g of solid. Recrystallization from CHCl$_3$ gave 5.34 g of shiny plates, m.p. 131°–132°.

$^1$H nmr $\delta_{acetone-d_6}^{TMS}$ 8.33–7.47 (m. featuring s at 8.00), 7.30–6.87 (brds). Mass spec: measured 238.9560. Calc'd. for C$_7$H$_7$Cl$_2$NO$_2$S, 238.9574.

EXAMPLE 12

2-(Bromomethyl)benzenesulfonyl chloride

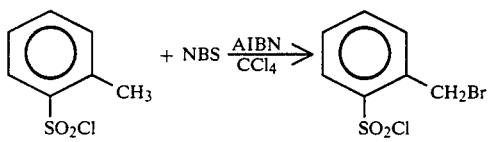

A solution of toluenesulfonyl chloride (4.5 g, ca. 85/15 mixture of ortho/para isomers) in carbon tetrachloride (40 ml) was contacted with N-bromosuccinimide (4.3 g) and azobisisobutyronitrile (50 mg) and heated to reflux for 22 hrs. The cooled mixture was filtered and the solvent was evaporated to give 6.33 g of yellow oil. Kugelrohr distillation provided 4.31 g, b.p. 90°–98° (0.2 mm). $^1$H nmr $\delta_{CDCl_3}^{TMS}$ 8.46–7.25 (m), 5.0 (s, area 47), 4.58 (s, area 12), 2.76 and 2.47 (singlets for unchanged toluenesulfonyl chloride contaminant). The ortho/para ratio of bromomethyl compounds was 80/20.

EXAMPLE 13

2-(Hydroxymethyl)benzenesulfonic acid, sodium salt

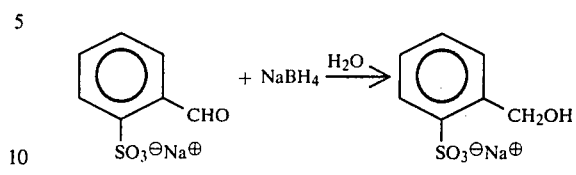

A solution of o-benzaldehydesulfonic acid, sodium salt (120 g) in water (2 l) was contacted in portions with sodium borohydride (21.6 g) and the solution was stirred for 48 hrs. The pH of the solution was adjusted to 7.0 by addition of hydrochloric acid. Water was removed under reduced pressure, and the residue was added to a large thimble and continuously extracted with ethanol. Concentration and cooling provided 102 g. of white solid, m.p. >300°. Evaporation of the mother liquor gave an additional 13.4 g of product.

$^1$H nmr $\delta_{D_2O}^{DSS}$ 8.10–7.85 (m), 7.77–7.26 (m). 5.13 (s), 4.70 (s).

EXAMPLE 14

2-(Chloromethyl)benzenesulfonyl chloride

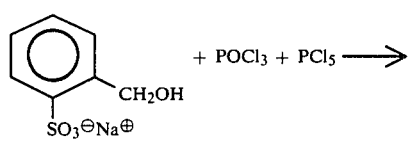

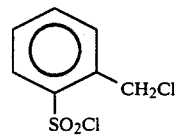

2-(Hydroxymethyl)benzenesulfonic acid, sodium salt (76 g) was contacted with phosphorus oxychloride (375 ml) and the stirred mixture was treated in portions with phosphorus pentachloride (76 g). The mixture was heated at 60°–70° for two days. Phosphorus oxychloride was removed under vacuum and the residue was treated with toluene (700 ml) and decanted into water. The organic layer was washed with water and brine, dried (MgSO$_4$) and evaporated. The product was kugelrohr distilled 90°–100°, 0.2 mm) to give 56 g of white solid, m.p. 43°–45°.

$^1$H nmr: $\delta_{COCl_3}^{TMS}$ 8.17–8.00 (m), 7.90–7.40 (m), 5.10 (s).

EXAMPLE 15

2-(Chloromethyl)benzenesulfonamide

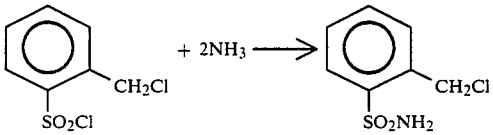

A solution of ammonia (5.2 ml) in tetrahydrofuran (250 ml) at −70° was contacted rapidly with a solution of 2-(chloromethyl)benzenesulfonyl chloride (21.8 g) in tetrahydrofuran (125 ml). The stirred mixture was allowed to warm to 0° and volatiles were removed under vacuum. The residue was contacted with ethyl acetate and a small volume of water. The organic layer was dried (MgSO₄) and evaporated to give 19.8 g of white solid, m.p. 156°–157.5°. Recrystallization from toluene-/ethyl acetate gave a sample with m.p. 157°–160°.

¹H nmr $\delta_{(CD_3)_2CO}^{TMS}$ 8.16–7.35 (m), 6.75 brds), 5.20 (s), 3.08 (s).

EXAMPLE 16
2-(1-Chloroethyl)benzenesulfonamide

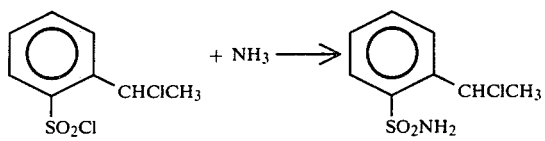

A solution of ammonia (1.2 ml) in tetrahydrofuran (100 ml) at −70° was contacted rapidly with a solution of 2-(1-chloroethyl)benzenesulfonyl chloride (4.32 g, 18.1 mmol) in tetrahydrofuran (50 ml). The stirred mixture was allowed to warm to 0° and volatiles were removed under reduced pressure. The residue was taken up in ethyl acetate and washed with a small volume of water and brine. The dried (MgSO₄) solution was evaporated to give 4.7 g of off white solid which was recrystallized from chloroform to give 3.13 g, m.p. 121°–122°.

¹H nmr $\delta_{(CD_3)_2CO}^{TMS}$ 8.25–7.30 (m), 6.93 (brds), 6.25 (q, J=7 Hz), 3.17 (s), 1.98 (d, J=7 Hz).

EXAMPLE 17
2-(Bromomethyl)benzenesulfonamide

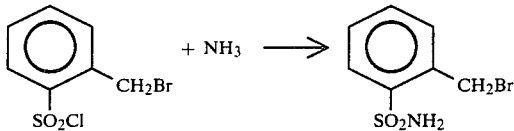

A solution of ammonia (1.0 ml) in tetrahydrofuran (50 ml) at −78° was contacted dropwise with a solution of a 60/40 mixture of 2-(bromomethyl)benzenesulfonyl chloride/4-(bromomethyl)benzenesulfonyl chloride (4.52 g) in tetrahydrofuran (20 ml). The stirred mixture was allowed to warm to 0° and volatiles were removed in vacuo. The residue was contacted with water (50 ml) and extracted three times with ethyl acetate. Combined organic portions were washed with brine, dried, and evaporated to give 4.00 g of white solid.

¹H nmr $\delta_{(CD_3)_2CO}^{TMS}$ 8.15–7.20 (m), 6.7–6.3 (m, NH), 4.95 (q, area 21), 4.55 (s, area 18), consistent with a ca. 60/40 mixture of 2-(bromomethyl)-/4-(bromomethyl)-benzenesulfonamides. The sample was fractionally recrystallized from chloroform, but without significant change in isomeric content.

EXAMPLE 18
2-(1-Pyrrolidinylmethyl)benzenesulfonamide

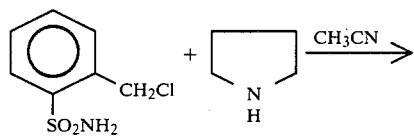

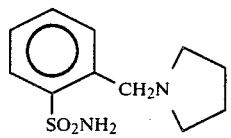

A solution of 2-(chloromethyl)benzenesulfonamide (2.00 g, 10 mmol) in acetonitrile (20 ml) was contacted with pyrrolidine (1.6 ml, 20 mmol). After 1.0 hr at ambient temperature, the volatiles were removed under vacuum and the residue was treated with water (40 ml) and chilled. The resulting solid was pulverized, filtered, and dried to give 2.23 g of white solid, m.p. 110°–112°.

Anal. Found C, 55.14; H, 6.71; N, 11.40; C, 54.66; H, 6.49; N, 11.49. Calc'd for C₁₁H₁₆N₂O₂S: C, 54.97; H, 6.71; N, 11.66.

EXAMPLE 19
2-(1-Pyrrolidinylmethyl)benzenesulfonamide, methyl iodide salt

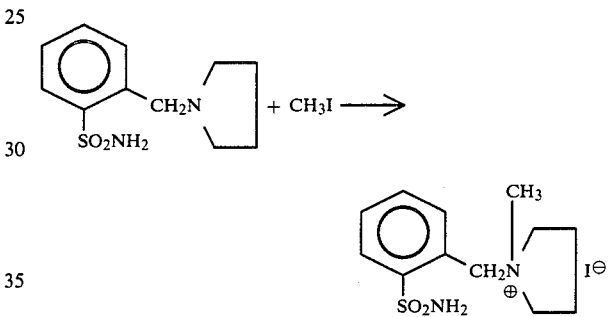

A solution of 2-(pyrrolidinomethyl)benzenesulfonamide (0.8 g) in acetonitrile (10 ml) was contacted with methyl iodide (3 ml) and heated to reflux for 2.0 hrs. Solvent was removed and the residue was treated with acetone and ether. The solid was filtered, digested with acetone (20 ml), chilled, and collected. There was obtained 1.00 g of white solid.

¹H nmr $\delta_{DMSO-d_6}^{TMS}$ 8.15–7.30 (m), 5.07 (s, 2H), 3.9–3.3 (m, 4H), 2.90 (s, 3H), 2.4–1.8 (m, 4H).

EXAMPLE 20
2-(Chloromethyl)-N-(butylaminocarbonyl)benzenesulfonamide

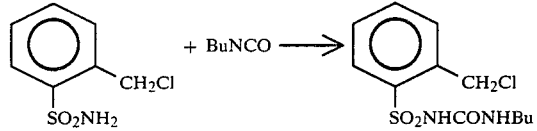

A mixtue of 2-(chloromethyl)benzenesulfonamide (13.2 g, 64 mmol) and butyl isocyanate (7.0 g, 71 mmol) in xylene (80 ml) was contacted with diazabicyclo[2.2.2]-octane (0.25 g) and heated to reflux for 5.0 hrs. Volatiles were removed under vacuum and the residue was treated with 0.5N NaOH (200 ml) and extracted with ethyl acetate (75 ml). The aqueous layer was separated, chilled, acidified (pH 4) with hydrochloric acid, and extracted with ethyl acetate. The organic layer was washed with brine, dried (MgSO₄), and evaporated to give 14.6 g of white solid. A sample was recrystallized from toluene to give m.p. 104°–106°.

$^1$H nmr $\delta_{CDCl_3}{}^{TMS}$ 9.5–8.1 (brds), 8.05–7.10 (m), 6.28 (t, J=2 Hz), 4.91 (s), 3.25–2.95 (m), 1.70–0.70 (m).

Examplary compounds within structure I that can be made by one or more of the described methods (Examples 1–9) are listed in Table I and II.

TABLE I

[Structure: phenyl ring with R substituent and C(R_1)(R_2)-L group ortho to -SO_2NHCNH- linked to pyrimidine ring with X, Y, Z substituents]

| L | R | R$_1$ | R$_2$ | X | Y | Z | m.p. (°C.) |
|---|---|---|---|---|---|---|---|
| Cl | H | H | H | CH$_3$ | CH$_3$ | CH | 176–177° |
| Br | H | H | H | CH$_3$ | CH$_3$ | CH | |
| pyrrolidinyl (N) | H | H | H | CH$_3$ | CH$_3$ | CH | |
| N-methylpyrrolidinium (⊕N-CH$_3$) | H | H | H | CH$_3$ | CH$_3$ | CH | |
| ⊕N(CH$_3$)$_3$ | H | H | H | CH$_3$ | CH$_3$ | CH | |
| NHCOCH$_3$ | H | H | H | CH$_3$ | CH$_3$ | CH | |
| NHCOCH$_2$CH$_3$ | H | H | H | CH$_3$ | CH$_3$ | CH | |
| N(CH$_3$)COCH$_3$ | H | H | H | CH$_3$ | CH$_3$ | CH | |
| NHCONH$_2$ | H | H | H | CH$_3$ | CH$_3$ | CH | |
| NHCONHCH$_3$ | H | H | H | CH$_3$ | CH$_3$ | CH | |
| N(CH$_3$)CNHCH$_3$ | H | H | H | CH$_3$ | CH$_3$ | CH | |
| NHCOCH$_3$ | H | H | H | CH$_3$ | CH$_3$ | CH | |
| NHCOCH$_2$H$_3$ | H | H | H | CH$_3$ | CH$_3$ | CH | |
| N(CH$_3$)COCH$_3$ | H | H | H | CH$_3$ | CH$_3$ | CH | |
| N(C$_2$H$_5$)COCH$_3$ | H | H | H | CH$_3$ | CH$_3$ | CH | |
| N(C$_4$H$_9$)COCH$_3$ | H | H | H | CH$_3$ | CH$_3$ | CH | |
| N(C$_4$H$_9$)COCH$_2$CH$_3$ | H | H | H | CH$_3$ | CH$_3$ | CH | |

TABLE I-continued

[Structure: benzene ring with R substituent, C(R₁)(R₂)L group, and SO₂NHC(=O)NH- linked to a pyrimidine/triazine ring with X, Y, Z substituents]

| L | R | R₁ | R₂ | X | Y | Z | m.p. (°C.) |
|---|---|----|----|---|---|---|------------|
| N(CH₃)₂ | H | H | H | CH₃ | CH₃ | CH | |
| N(CH₃)(C₂H₅) | H | H | H | CH₃ | CH₃ | CH | |
| N(C₂H₅)₂ | H | H | H | CH₃ | CH₃ | CH | |
| N(C₃H₇)₂ | H | H | H | CH₃ | CH₃ | CH | |
| piperidino | H | H | H | CH₃ | CH₃ | CH | |
| morpholino | H | H | H | CH₃ | CH₃ | CH | |
| N(OCH₃)CH₃ | H | H | H | CH₃ | CH₃ | CH | |
| NH₂ | H | H | H | CH₃ | CH₃ | CH | |
| NHCH₃ | H | H | H | CH₃ | CH₃ | CH | |
| F | H | H | H | CH₃ | CH₃ | CH | |
| F | H | H | H | CH₃ | CH₃ | N | |
| F | H | H | H | CH₃ | OCH₃ | CH | |
| F | H | H | H | CH₃ | OCH₃ | N | |
| F | H | H | H | OCH₃ | OCH₃ | CH | |
| F | H | H | H | OCH₃ | OCH₃ | N | |
| F | H | H | H | CH₃ | CH₂OCH₃ | CH | |
| F | H | H | H | OCH₃ | CH₂OCH₃ | N | |
| F | H | H | H | Cl | OCH₃ | CH | |
| Cl | H | H | H | CH₃ | Cl | CH | |
| Br | H | H | H | CH₃ | Cl | CH | |
| pyrrolidino | H | H | H | CH₃ | Cl | CH | |
| N-methylpyrrolidinium | H | H | H | CH₃ | Cl | CH | |
| ⊕N(CH₃)₃ | H | H | H | CH₃ | Cl | CH | |
| NHC(=O)CH₃ | H | H | H | CH₃ | Cl | CH | |
| F | H | F | H | CH₃ | CH₃ | CH | |
| F | H | F | H | CH₃ | OCH₃ | CH | |
| F | H | F | H | OCH₃ | OCH₃ | CH | |
| F | H | F | H | OCH₃ | OCH₃ | N | |
| F | H | F | H | CH₃ | OCH₃ | N | |
| F | H | F | H | CH₃ | CH₃ | N | |
| F | H | F | H | Cl | CH₃ | CH | |
| NHC₄H₉ | H | H | H | CH₃ | CH₃ | CH | |
| N(CH₃)(n-C₄H₉) | H | H | H | CH₃ | CH₃ | CH | |

TABLE I-continued

[Structure: benzene ring with R substituent, C(R1)(R2)-L group ortho, and -SO2NHC(=O)NH- linked to pyrimidine ring with X, Y, Z substituents]

| L | R | R₁ | R₂ | X | Y | Z | m.p. (°C.) |
|---|---|---|---|---|---|---|---|
| −N⁺(pyrrolidine)−C₂H₅ | H | H | H | CH₃ | CH₃ | CH | |
| NHC(O)CH₂CH₃ | H | H | H | CH₃ | CH₃ | CH | |
| NHC(O)C₄H₉ | H | H | H | CH₃ | CH₃ | CH | |
| NHC(O)CF₃ | H | H | H | CH₃ | CH₃ | CH | |
| NHC(O)CH₂Cl | H | H | H | CH₃ | CH₃ | CH | |
| NHC(O)CCL₃ | H | H | H | CH₃ | CH₃ | CH | |
| N(CH₃)C(O)CH₂BR | H | H | H | CH₃ | CH₃ | CH | |
| N(C₂H₅)C(O)NHCH₂CH₃ | H | H | H | CH₃ | CH₃ | CH | |
| N(n-C₃H₇)C(O)NHCH(CH₃)₂ | H | H | H | CH₃ | CH₃ | CH | |
| N(n-C₄H₉)C(O)NHC₄H₉ | H | H | H | CH₃ | CH₃ | CH | |
| NHC(O)OCH(CH₃)₂ | H | H | H | CH₃ | CH₃ | CH | |
| NHC(O)On-C₄H₉ | H | H | H | CH₃ | CH₃ | CH | |
| Cl | H | CH₃ | H | CH₃ | CH₃ | CH | |
| Cl | H | CH₂CH₂CH₃ | H | CH₃ | CH₃ | CH | |
| Cl | H | n-C₄H₉ | H | CH₃ | CH₃ | CH | |
| Cl | H | H | H | CH₃ | CH₃ | C—Cl | |
| Cl | H | H | H | CH₃ | CH₃ | C—Br | |
| Cl | H | H | H | CH₃ | CH₃ | C—CN | |
| Cl | H | H | H | CH₃ | CH₃ | C—CH₃ | |
| Cl | H | H | H | CH₃ | CH₃ | C—CH₂CH₃ | |
| Cl | H | H | H | CH₃ | CH₃ | C—CH₂Cl | |
| Cl | H | H | H | CH₃ | CH₃ | C—CH₂CH=CH₂ | |
| Cl | 5-F | H | H | CH₃ | CH₃ | CH | |
| Cl | 5-Br | H | H | CH₃ | CH₃ | CH | |
| Cl | 5-CH₃ | H | H | CH₃ | CH₃ | CH | |
| Cl | 5-CH₂CH₂CH₃ | H | H | CH₃ | CH₃ | CH | |
| Cl | 5-OCH₃ | H | H | CH₃ | CH₃ | CH | |
| Cl | 5-OCH(CH₃)₂ | H | H | CH₃ | CH₃ | CH | |
| Cl | CF₃ | H | H | CH₃ | CH₃ | CH | |
| Cl | H | H | H | CH₃ | OCH₃ | CH | |
| Br | H | H | H | CH₃ | OCH₃ | CH | |

TABLE I-continued

| L | R | R₁ | R₂ | X | Y | Z | m.p. (°C.) |
|---|---|---|---|---|---|---|---|
| 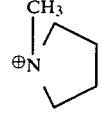 | | H | H | H | CH₃ | OCH₃ | CH | |
|  | | H | H | H | CH₃ | OCH₃ | CH | |
| ⊕N(CH₃)₃ | H | H | H | CH₃ | OCH₃ | CH | |
| NHC(O)CH₃ | H | H | H | CH₃ | OCH₃ | CH | |
| Cl | H | H | H | H | CH₃ | CH | |
| Br | H | H | H | H | CH₃ | CH | |
| 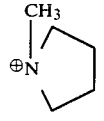 | | H | H | H | H | CH₃ | CH | |
|  | | H | H | H | H | CH₃ | CH | |
| ⊕N(CH₃)₃ | H | H | H | H | CH₃ | CH | |
| NHC(O)CH₃ | H | H | H | H | CH₃ | CH | |
| Cl | H | H | CH₃ | CH₃ | CH₃ | CH | |
| Br | H | H | CH₃ | CH₃ | CH₃ | CH | |
| 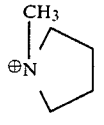 | | H | H | CH₃ | CH₃ | CH₃ | CH | |
| ⊕N(CH₃)(pyrrolidine) | H | H | CH₃ | CH₃ | CH₃ | CH | |
| ⊕N(CH₃)₃ | H | H | CH₃ | CH₃ | CH₃ | CH | |
| NHC(O)CH₃ | H | H | CH₃ | CH₃ | CH₃ | CH | |
| Cl | H | H | CH₃ | CH₃ | OCH₃ | CH | |
| Br | H | H | CH₃ | CH₃ | OCH₃ | CH | |

TABLE I-continued

Structure:

R—[phenyl with C(R1)(R2)—L substituent]—SO₂NHC(O)NH—[pyrimidine with X, Y, Z]

| L | R | R₁ | R₂ | X | Y | Z | m.p. (°C.) |
|---|---|----|----|---|---|---|------------|
| pyrrolidin-1-yl | H | H | CH₃ | CH₃ | OCH₃ | CH | |
| N-methylpyrrolidinium | H | H | CH₃ | CH₃ | OCH₃ | CH | |
| ⊕N(CH₃)₃ | H | H | CH₃ | CH₃ | OCH₃ | CH | |
| NHC(O)CH₃ | H | H | CH₃ | CH₃ | OCH₃ | CH | |
| Cl | H | H | H | OCH₃ | OCH₃ | CH | 192–193° |
| Br | H | H | H | OCH₃ | OCH₃ | CH | |
| pyrrolidin-1-yl | H | H | H | OCH₃ | OCH₃ | CH | 138–140° |
| N-methylpyrrolidinium | H | H | H | OCH₃ | OCH₃ | CH | |
| ⊕N(CH₃)₃ | H | H | H | OCH₃ | OCH₃ | CH | |
| NHC(O)CH₃ | H | H | H | OCH₃ | OCH₃ | CH | |
| NHC(O)CH₂CH₃ | H | H | H | OCH₃ | OCH₃ | CH | |
| N(CH₃)C(O)CH₃ | H | H | H | OCH₃ | OCH₃ | CH | |
| NHC(O)NH₂ | H | H | H | OCH₃ | OCH₃ | CH | |
| NHC(O)NHCH₃ | H | H | H | OCH₃ | OCH₃ | CH | |
| N(CH₃)C(O)NHCH₃ | H | H | H | OCH₃ | OCH₃ | CH | |
| NHC(O)OCH₃ | H | H | H | OCH₃ | OCH₃ | CH | |
| Cl | H | H | H | CH₃ | OCH₃ | OCH₃ | CH |
| Br | H | H | H | CH₃ | OCH₃ | OCH₃ | CH |

TABLE I-continued

| L | R | $R_1$ | $R_2$ | X | Y | Z | m.p. (°C.) |
|---|---|---|---|---|---|---|---|
| pyrrolidin-1-yl | H | H | $CH_3$ | $OCH_3$ | $OCH_3$ | CH | |
| 1-methylpyrrolidinium | H | H | $CH_3$ | $OCH_3$ | $OCH_3$ | CH | |
| $\overset{\oplus}{N}(CH_3)_3$ | H | H | $CH_3$ | $OCH_3$ | $OCH_3$ | CH | |
| $NHCOCH_3$ | H | H | $CH_3$ | $OCH_3$ | $OCH_3$ | CH | |
| Cl | 5-$NO_2$ | H | H | $CH_3$ | $CH_3$ | CH | |
| Br | 5-$NO_2$ | H | H | $CH_3$ | $CH_3$ | CH | |
| pyrrolidin-1-yl | 5-$NO_2$ | H | H | $CH_3$ | $CH_3$ | CH | |
| 1-methylpyrrolidinium | 5-$NO_2$ | H | H | $CH_3$ | $CH_3$ | CH | |
| $\overset{\oplus}{N}(CH_3)_3$ | 5-$NO_2$ | H | H | $CH_3$ | $CH_3$ | CH | |
| $NHCOCH_3$ | 5-$NO_2$ | H | H | $CH_3$ | $CH_3$ | CH | |
| Cl | 5-Cl | H | H | $CH_3$ | $CH_3$ | CH | |
| Br | 5-Cl | H | H | $CH_3$ | $CH_3$ | CH | |
| pyrrolidin-1-yl | 5-Cl | H | H | $CH_3$ | $CH_3$ | CH | |
| 1-methylpyrrolidinium | 5-Cl | H | H | $CH_3$ | $CH_3$ | CH | |
| $\overset{\oplus}{N}(CH_3)_3$ | 5-Cl | H | H | $CH_3$ | $CH_3$ | CH | |
| $NHCOCH_3$ | 5-Cl | H | H | $CH_3$ | $CH_3$ | CH | |
| Cl | 5-$NO_2$ | H | H | $CH_3$ | $OCH_3$ | CH | |
| Br | 5-$NO_2$ | H | H | $CH_3$ | $OCH_3$ | CH | |

TABLE I-continued

| L | R | R₁ | R₂ | X | Y | Z | m.p. (°C.) |
|---|---|---|---|---|---|---|---|
| pyrrolidinyl (N) | 5-NO₂ | H | H | CH₃ | OCH₃ | CH | |
| N-methylpyrrolidinium | 5-NO₂ | H | H | CH₃ | OCH₃ | CH | |
| ⊕N(CH₃)₃ | 5-NO₂ | H | H | CH₃ | OCH₃ | CH | |
| NHC(O)CH₃ | 5-NO₂ | H | H | CH₃ | OCH₃ | CH | |
| Cl | 5-Cl | H | H | CH₃ | OCH₃ | CH | |
| Br | 5-Cl | H | H | CH₃ | OCH₃ | CH | |
| pyrrolidinyl | 5-Cl | H | H | CH₃ | OCH₃ | CH | |
| N-methylpyrrolidinium | 5-Cl | H | H | CH₃ | OCH₃ | CH | |
| ⊕N(CH₃)₃ | 5-Cl | H | H | CH₃ | OCH₃ | CH | |
| NHC(O)CH₃ | 5-Cl | H | H | CH₃ | OCH₃ | CH | |
| Cl | 5-Cl | H | H | OCH₃ | OCH₃ | CH | |
| Br | 5-Cl | H | H | OCH₃ | OCH₃ | CH | |
| pyrrolidinyl | 5-Cl | H | H | OCH₃ | OCH₃ | CH | |
| N-methylpyrrolidinium | 5-Cl | H | H | OCH₃ | OCH₃ | CH | |
| ⊕N(CH₃)₃ | 5-Cl | H | H | OCH₃ | OCH₃ | CH | |
| NHC(O)CH₃ | | | | | | | |
| Cl | 5-NO₂ | H | H | OCH₃ | OCH₃ | CH | |
| Br | 5-NO₂ | H | H | OCH₃ | OCH₃ | CH | |

TABLE I-continued

[Structure: R-substituted phenyl with C(R₁)(R₂)-L group and SO₂NHC(O)NH- linker to pyrimidine/triazine ring with X, Y, Z substituents]

| L | R | R₁ | R₂ | X | Y | Z | m.p. (°C.) |
|---|---|----|----|---|---|---|------------|
| pyrrolidin-1-yl | 5-NO₂ | H | H | OCH₃ | OCH₃ | CH | |
| 1-methylpyrrolidinium | 5-NO₂ | H | H | OCH₃ | OCH₃ | CH | |
| ⊕N(CH₃)₃ | 5-NO₂ | H | H | OCH₃ | OCH₃ | CH | |
| NHC(O)CH₃ | 5-NO₂ | H | H | OCH₃ | OCH₃ | CH | |
| Cl | H | Cl | H | CH₃ | CH₃ | CH | 195–197° |
| Br | H | Cl | H | CH₃ | CH₃ | CH | |
| Cl | H | Cl | H | OCH₃ | CH₃ | CH | 189–190° |
| Cl | H | Cl | H | OCH₃ | OCH₃ | CH | |
| Br | H | Cl | H | OCH₃ | CH₃ | CH | |
| Br | H | Cl | H | OCH₃ | OCH₃ | CH | |
| Cl | 5-Cl | Cl | H | CH₃ | CH₃ | CH | |
| Cl | 5-NO₂ | Cl | H | CH₃ | CH₃ | CH | |
| Br | 5-Cl | Cl | H | CH₃ | CH₃ | CH | |
| Br | 5-NO₂ | Cl | H | CH₃ | CH₃ | CH | |
| Cl | 5-Cl | Cl | H | OCH₃ | CH₃ | CH | |
| Cl | 5-NO₂ | Cl | H | OCH₃ | CH₃ | CH | |
| Br | 5-Cl | Cl | H | OCH₃ | OCH₃ | CH | |
| Br | 5-NO₂ | Cl | H | OCH₃ | OCH₃ | CH | |
| Cl | 5-Cl | Cl | H | OCH₃ | OCH₃ | CH | |
| Cl | 5-NO₂ | Cl | H | OCH₃ | OCH₃ | CH | |
| Br | 5-Cl | Cl | H | OCH₃ | CH₃ | CH | |
| Br | 5-NO₂ | Cl | H | OCH₃ | CH₃ | CH | |
| Cl | H | H | H | CH₃ | CH₃ | N | |
| Br | H | H | H | CH₃ | CH₃ | N | |
| pyrrolidin-1-yl | H | H | H | CH₃ | CH₃ | N | |
| 1-methylpyrrolidinium | H | H | H | CH₃ | CH₃ | N | |
| ⊕N(CH₃)₃ | H | H | H | CH₃ | CH₃ | N | |
| NHC(O)CH₃ | H | H | H | CH₃ | CH₃ | N | |
| NHC(O)CH₂CH₃ | H | H | H | CH₃ | CH₃ | N | |
| N(CH₃)C(O)CH₃ | H | H | H | CH₃ | CH₃ | N | |

TABLE I-continued

| L | R | R₁ | R₂ | X | Y | Z | m.p. (°C.) |
|---|---|----|----|---|---|---|------------|
| NHCNH₂ (C=O) | H | H | H | CH₃ | CH₃ | N | |
| NHCNHCH₃ (C=O) | H | H | H | CH₃ | CH₃ | N | |
| N(CH₃)CNHCH₃ (C=O) | H | H | H | CH₃ | CH₃ | N | |
| NHCOCH₃ (C=O) | H | H | H | CH₃ | CH₃ | N | |
| Cl | H | H | H | CH₃ | Cl | N | |
| Br | H | H | H | CH₃ | Cl | N | |
| pyrrolidin-1-yl | H | H | H | CH₃ | Cl | N | |
| N-methylpyrrolidinium | H | H | H | CH₃ | Cl | N | |
| ⊕N(CH₃)₃ | H | H | H | CH₃ | Cl | N | |
| NHCCH₃ (C=O) | H | H | H | CH₃ | Cl | N | |
| Cl | H | H | H | CH₃ | OCH₃ | N | |
| Br | H | H | H | CH₃ | OCH₃ | N | |
| pyrrolidin-1-yl | H | H | H | CH₃ | OCH₃ | N | |
| N-methylpyrrolidinium | H | H | H | CH₃ | OCH₃ | N | |
| ⊕N(CH₃)₃ | H | H | H | CH₃ | OCH₃ | N | |
| NHCCH₃ (C=O) | H | H | H | CH₃ | OCH₃ | N | |
| Cl | H | H | H | H | CH₃ | N | |
| Br | H | H | H | H | CH₃ | N | |
| pyrrolidin-1-yl | H | H | H | H | CH₃ | N | |

TABLE I-continued

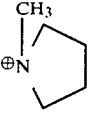

| L | R | R₁ | R₂ | X | Y | Z | m.p. (°C.) |
|---|---|---|---|---|---|---|---|
|  (N-methyl pyrrolidinium) | H | H | H | H | CH₃ | N | |
| ⊕N(CH₃)₃ | H | H | H | H | CH₃ | N | |
| NHCOCH₃ | H | H | H | H | CH₃ | N | |
| Cl | H | H | CH₃ | CH₃ | CH₃ | N | |
| Br | H | H | CH₃ | CH₃ | CH₃ | N | |
| 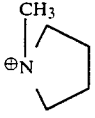 (pyrrolidinyl) | H | H | CH₃ | CH₃ | CH₃ | N | |
|  (N-methyl pyrrolidinium) | H | H | CH₃ | CH₃ | CH₃ | N | |
| ⊕N(CH₃)₃ | H | H | CH₃ | CH₃ | CH₃ | N | |
| NHCOCH₃ | H | H | CH₃ | CH₃ | CH₃ | N | |
| Cl | H | H | CH₃ | CH₃ | OCH₃ | N | |
| Br | H | H | CH₃ | CH₃ | OCH₃ | N | |
| 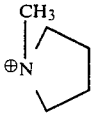 (pyrrolidinyl) | H | H | CH₃ | CH₃ | OCH₃ | N | |
|  (N-methyl pyrrolidinium) | H | H | CH₃ | CH₃ | OCH₃ | N | |
| ⊕N(CH₃)₃ | H | H | CH₃ | CH₃ | OCH₃ | N | |
| NHCOCH₃ | H | H | CH₃ | CH₃ | OCH₃ | N | |
| Cl | H | H | H | OCH₃ | OCH₃ | N | 150–152° |
| Br | H | H | H | OCH₃ | OCH₃ | N | |
| pyrrolidinyl | H | H | H | OCH₃ | OCH₃ | N | |

TABLE I-continued $$\text{structure with } R, R_1, R_2, C-L, SO_2NHCNH-, \text{pyrimidine with } X, Y, Z$$

| L | R | $R_1$ | $R_2$ | X | Y | Z | m.p. (°C.) |
|---|---|---|---|---|---|---|---|
| N-methylpyrrolidinium (⊕N-CH₃) | H | H | H | OCH₃ | OCH₃ | N | |
| ⊕N(CH₃)₃ | H | H | H | OCH₃ | OCH₃ | N | |
| NHC(O)CH₃ | H | H | H | OCH₃ | OCH₃ | N | |
| NHC(O)CH₂CH₃ | H | H | H | OCH₃ | OCH₃ | N | |
| N(CH₃)C(O)CH₃ | H | H | H | OCH₃ | OCH₃ | N | |
| NHC(O)NH₂ | H | H | H | OCH₃ | OCH₃ | N | |
| NHC(O)NHCH₃ | H | H | H | OCH₃ | OCH₃ | N | |
| NH(CH₃)C(O)NHCH₃ | H | H | H | OCH₃ | OCH₃ | N | |
| NHC(O)OCH₃ | H | H | H | OCH₃ | OCH₃ | N | |
| Cl | H | H | CH₃ | OCH₃ | OCH₃ | N | 148–150° |
| Br | H | H | CH₃ | OCH₃ | OCH₃ | N | |
| pyrrolidinyl (N) | H | H | CH₃ | OCH₃ | OCH₃ | N | |
| N-methylpyrrolidinium (⊕N-CH₃) | H | H | CH₃ | OCH₃ | OCH₃ | N | |
| ⊕N(CH₃)₃ | H | H | CH₃ | OCH₃ | OCH₃ | N | |
| NHC(O)CH₃ | H | H | CH₃ | OCH₃ | OCH₃ | N | |
| NHC(O)CH₂CH₃ | H | H | CH₃ | OCH₃ | OCH₃ | N | |
| N(CH₃)C(O)CH₃ | H | H | CH₃ | OCH₃ | OCH₃ | N | |
| NHC(O)NH₂ | H | H | CH₃ | OCH₃ | OCH₃ | N | |

TABLE I-continued

| L | R | R₁ | R₂ | X | Y | Z | m.p. (°C.) |
|---|---|---|---|---|---|---|---|
| NHC(O)NHCH₃ | H | H | CH₃ | OCH₃ | OCH₃ | N | |
| N(CH₃)C(O)NHCH₃ | H | H | CH₃ | OCH₃ | OCH₃ | N | |
| NHC(O)OCH₃ | H | H | CH₃ | OCH₃ | OCH₃ | N | |
| Cl | 5-NO₂ | H | H | CH₃ | CH₃ | N | |
| Br | 5-NO₂ | H | H | CH₃ | CH₃ | N | |
| pyrrolidinyl | 5-NO₂ | H | H | CH₃ | CH₃ | N | |
| N-methylpyrrolidinium | 5-NO₂ | H | H | CH₃ | CH₃ | N | |
| ⁺N(CH₃)₃ | 5-NO₂ | H | H | CH₃ | CH₃ | N | |
| NHC(O)CH₃ | 5-NO₂ | H | H | CH₃ | CH₃ | N | |
| Cl | 5-Cl | H | H | CH₃ | CH₃ | N | |
| Br | 5-Cl | H | H | CH₃ | CH₃ | N | |
| pyrrolidinyl | 5-Cl | H | H | CH₃ | CH₃ | N | |
| N-methylpyrrolidinium | 5-Cl | H | H | CH₃ | CH₃ | N | |
| ⁺(CH₃)₃ | 5-Cl | H | H | CH₃ | CH₃ | N | |
| NHC(O)CH₃ | 5-Cl | H | H | CH₃ | CH₃ | N | |
| Cl | 5-NO₂ | H | H | CH₃ | OCH₃ | N | |
| Br | 5-NO₂ | H | H | CH₃ | OCH₃ | N | |
| pyrrolidinyl | 5-NO₂ | H | H | CH₃ | OCH₃ | N | |

TABLE I-continued

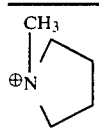

| L | R | R₁ | R₂ | X | Y | Z | m.p. (°C.) |
|---|---|----|----|---|---|---|------------|
| $\overset{CH_3}{\underset{\oplus N}{|}}$ (pyrrolidinium) | 5-NO₂ | H | H | CH₃ | OCH₃ | N | |
| $\overset{\oplus}{N}(CH_3)_3$ | 5-NO₂ | H | H | CH₃ | OCH₃ | N | |
| NHCCH₃ (O=) | 5-NO₂ | H | H | CH₃ | OCH₃ | N | |
| Cl | 5-Cl | H | H | CH₃ | OCH₃ | N | |
| Br | 5-Cl | H | H | CH₃ | OCH₃ | N | |
| pyrrolidine (N) | 5-Cl | H | H | CH₃ | OCH₃ | N | |
| $\overset{CH_3}{\underset{\oplus N}{|}}$ | 5-Cl | H | H | CH₃ | OCH₃ | N | |
| $\overset{\oplus}{N}(CH_3)_3$ | 5-Cl | H | H | CH₃ | OCH₃ | N | |
| NHCCH₃ (O=) | 5-Cl | H | H | CH₃ | OCH₃ | N | |
| Cl | 5-NO₂ | H | H | OCH₃ | OCH₃ | N | |
| Br | 5-NO₂ | H | H | OCH₃ | OCH₃ | N | |
| pyrrolidine (N) | 5-NO₂ | H | H | OCH₃ | OCH₃ | N | |
| $\overset{CH_3}{\underset{\oplus N}{|}}$ | 5-NO₂ | H | H | OCH₃ | OCH₃ | N | |
| $\overset{\oplus}{N}(CH_3)_3$ | 5-NO₂ | H | H | OCH₃ | OCH₃ | N | |
| NHCCH₃ (O=) | 5-NO₂ | H | H | OCH₃ | OCH₃ | N | |
| Cl | 5-Cl | H | H | OCH₃ | OCH₃ | N | |
| Br | 5-Cl | H | H | OCH₃ | OCH₃ | N | |
| pyrrolidine (N) | 5-Cl | H | H | OCH₃ | OCH₃ | N | |

TABLE I-continued

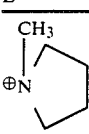

| L | R | R₁ | R₂ | X | Y | Z | m.p. (°C.) |
|---|---|----|----|---|---|---|------------|
| $\overset{CH_3}{\underset{\oplus N}{\mid}}$⟨pyrrolidine⟩ | 5-Cl | H | H | CH₃ | OCH₃ | N | |
| $\overset{\oplus}{N}(CH_3)_3$ | 5-Cl | H | H | OCH₃ | OCH₃ | N | |
| $\overset{O}{\underset{NHCCH_3}{\parallel}}$ | 5-Cl | H | H | OCH₃ | OCH₃ | N | |
| Cl | H | Cl | H | CH₃ | CH₃ | N | |
| Br | H | Cl | H | CH₃ | CH₃ | N | |
| Cl | H | Cl | H | OCH₃ | CH₃ | N | 168–169° |
| Cl | H | Cl | H | OCH₃ | OCH₃ | N | |
| Br | H | Cl | H | OCH₃ | CH₃ | N | |
| Br | H | Cl | H | OCH₃ | OCH₃ | N | |
| Cl | 5-Cl | Cl | H | CH₃ | CH₃ | N | |
| Cl | 5-NO₂ | Cl | H | CH₃ | CH₃ | N | |
| Br | 5-Cl | Cl | H | CH₃ | CH₃ | N | |
| Br | 5-NO₂ | Cl | H | CH₃ | CH₃ | N | |
| Cl | 5-Cl | Cl | H | OCH₃ | CH₃ | N | |
| Cl | 5-NO₂ | Cl | H | OCH₃ | CH₃ | N | |
| Br | 5-Cl | Cl | H | OCH₃ | OCH₃ | N | |
| Br | 5-NO₂ | Cl | H | OCH₃ | OCH₃ | N | |
| Cl | 5-Cl | Cl | H | OCH₃ | OCH₃ | N | |
| Cl | 5-NO₂ | Cl | H | OCH₃ | OCH₃ | N | |
| Br | 5-Cl | Cl | H | OCH₃ | CH₃ | N | |
| Br | 5-NO₂ | Cl | H | OCH₃ | CH₃ | N | |

TABLE II

| L | R | R₁ | R₂ | R₈ | W | X | Y | Z | m.p. (°C.) |
|---|---|----|----|----|----|---|---|---|------------|
| Cl | H | H | H | CH₃ | O | CH₃ | CH₃ | CH | |
| Cl | H | H | H | CH₃ | O | OCH₃ | CH₃ | CH | |
| Cl | H | H | H | CH₃ | O | OCH₃ | OCH₃ | CH | |
| Cl | H | H | H | CH₃ | O | CH₃ | CH₃ | N | |
| Cl | H | H | H | CH₃ | O | CH₃ | OCH₃ | N | |
| Cl | H | H | H | CH₃ | O | OCH₃ | OCH₃ | N | |
|  | H | H | H | CH₃ | O | CH₃ | CH₃ | CH | |
|  | H | H | H | CH₃ | O | OCH₃ | CH₃ | CH | |

TABLE II-continued

| L | R | R₁ | R₂ | R₈ | W | X | Y | Z | m.p. (°C.) |
|---|---|----|----|----|----|---|---|---|------------|
|  | H | H | H | CH₃ | O | OCH₃ | OCH₃ | CH | |
|  | H | H | H | CH₃ | O | CH₃ | CH₃ | N | |
| (pyrrolidinyl) | H | H | H | CH₃ | O | OCH₃ | CH₃ | N | |

TABLE II-continued

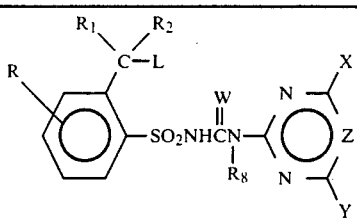

| L | R | R₁ R₂ R₈ | W | X | Y | Z | m.p. (°C.) |
|---|---|---|---|---|---|---|---|
| (pyrrolidinyl-N) | H | H H CH₃ | O | OCH₃ | OCH₃ | N | |
| NHC(O)CH₃ | H | H H CH₃ | O | CH₃ | CH₃ | CH | |
| NHC(O)CH₃ | H | H H CH₃ | O | CH₃ | OCH₃ | CH | |
| NHC(O)CH₃ | H | H H CH₃ | O | OCH₃ | OCH₃ | CH | |
| NHC(O)CH₃ | H | H H CH₃ | O | CH₃ | CH₃ | N | |
| NHC(O)CH₃ | H | H H CH₃ | O | OCH₃ | CH₃ | N | |
| NHC(O)CH₃ | H | H H CH₃ | O | OCH₃ | OCH₃ | N | |
| —N⊕(CH₃)₃ | H | H H CH₃ | O | OCH₃ | OCH₃ | CH | |
| —NHC(O)NHCH₃ | H | H H CH₃ | O | OCH₃ | OCH₃ | CH | |
| Cl | H | H H H | S | CH₃ | CH₃ | CH | |
| Cl | H | H H H | S | OCH₃ | CH₃ | CH | |
| Cl | H | H H H | S | OCH₃ | OCH₃ | CH | |
| Cl | H | H H H | S | OCH₃ | CH₃ | N | |
| Cl | H | H H H | S | OCH₃ | OCH₃ | N | |
| Cl | H | H H OCH₃ | O | CH₃ | CH₃ | CH | |
| Cl | H | H H OCH₃ | O | CH₃ | OCH₃ | CH | |
| Cl | H | H H OCH₃ | O | OCH₃ | OCH₃ | CH | |
| Cl | H | H H OCH₃ | O | CH₃ | CH₃ | N | |

TABLE II-continued

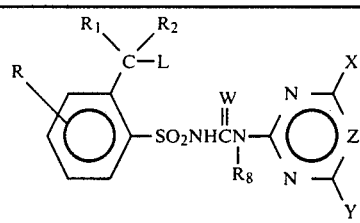

| L | R | R₁ R₂ R₈ | W | X | Y | Z | m.p. (°C.) |
|---|---|---|---|---|---|---|---|
| Cl | H | H H H OCH₃ | O | CH₃ | OCH₃ | N | |
| Cl | H | H H H OCH₃ | O | OCH₃ | OCH₃ | N | |
| (pyrrolidinyl-N) | H | H H OCH₃ | O | CH₃ | CH₃ | CH | |
| (pyrrolidinyl-N) | H | H H OCH₃ | O | CH₃ | OCH₃ | CH | |
| (pyrrolidinyl-N) | H | H H OCH₃ | O | OCH₃ | OCH₃ | CH | |
| (pyrrolidinyl-N) | H | H H OCH₃ | O | CH₃ | CH₃ | N | |
| (pyrrolidinyl-N) | H | H H OCH₃ | O | CH₃ | OCH₃ | N | |
| (pyrrolidinyl-N) | H | H H OCH₃ | O | OCH₃ | OCH₃ | N | |
| F | H | H H CH₃ | O | CH₃ | OCH₃ | N | |
| F | H | H H CH₃ | O | OCH₃ | OCH₃ | CH | |
| F | H | H H CH₃ | O | OCH₃ | OCH₃ | N | |

TABLE III

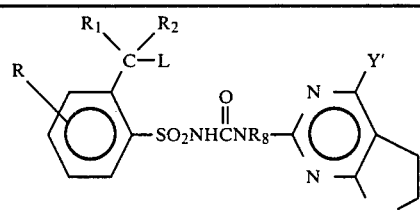

| R | R₁ | R₂ | R₈ | Y' | Q | L |
|---|---|---|---|---|---|---|
| H | H | H | H | CH₃ | O | Cl |
| H | H | H | H | CH₃O | O | Cl |
| H | H | H | H | Cl | O | Cl |
| H | H | H | H | H | O | Cl |
| H | H | H | H | CH₃ | CH₂ | Cl |
| H | H | H | H | CH₃O | CH₂ | Cl |
| H | Cl | H | H | CH₃ | O | Cl |
| H | Cl | H | H | CH₃O | O | Cl |
| H | Cl | H | H | Cl | O | Cl |
| H | Cl | H | H | H | O | Cl |
| H | Cl | H | H | CH₃ | CH₂ | Cl |
| H | Cl | H | H | CH₃O | CH₂ | Cl |

TABLE III-continued
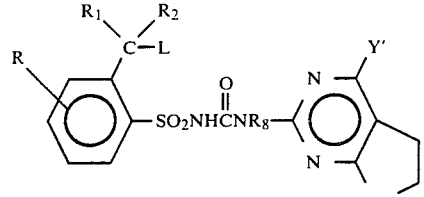
| | | | | | | |
|---|---|---|---|---|---|---|
| H | H | H | H | CH$_3$ | O | Br |
| H | H | H | H | CH$_3$O | O | Br |
| H | H | H | H | Cl | O | Br |
| H | H | H | H | H | O | Br |
| H | H | H | H | CH$_3$ | CH$_2$ | Br |
| H | H | H | H | CH$_3$O | CH$_2$ | Br |
| H | H | H | H | CH$_3$ | O |  |
| H | H | H | H | CH$_3$O | O |  |
| H | H | H | H | Cl | O |  |
| H | H | H | H | H | O |  |
| H | H | H | H | CH$_3$ | CH$_2$ |  |
| H | H | H | H | CH$_3$O | CH$_2$ |  |
| H | H | H | H | CH$_3$ | O | 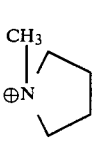 |
| H | H | H | H | CH$_3$O | O | 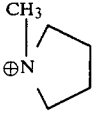 |
| H | H | H | H | Cl | O | 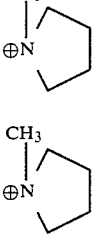 |
| H | H | H | H | H | O |  |

TABLE III-continued

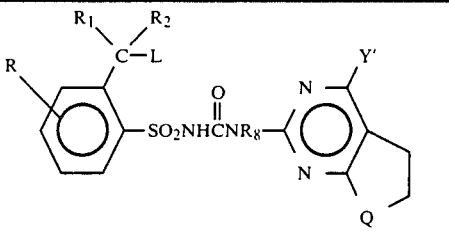

| R | R1 | R2 | L | X | Z | Q |
|---|---|---|---|---|---|---|
| H | H | H | H | CH3 | CH2 | CH3–⊕N(pyrrolidine) |
| H | H | H | H | CH3O | CH2 | CH3–⊕N(pyrrolidine) |
| H | H | H | H | CH3 | O | +NMe3 |
| H | H | H | H | CH3O | O | +NMe3 |
| H | H | H | H | Cl | O | +NMe3 |
| H | H | H | H | H | O | +NMe3 |
| H | H | H | H | CH3 | CH2 | +NMe3 |
| H | H | H | H | CH3O | CH2 | +NMe3 |
| H | H | H | H | CH3 | O | NH2 |
| H | H | H | H | CH3O | O | NH2 |
| H | H | H | H | Cl | O | NH2 |
| H | H | H | H | H | O | NH2 |
| H | H | H | H | CH3 | CH2 | NH2 |
| H | H | H | H | CH3O | CH2 | NH2 |
| H | H | H | H | CH3 | O | NHCOCH3 |
| H | H | H | H | CH3O | O | NHCOCH3 |
| H | H | H | H | Cl | O | NHCOCH3 |
| H | H | H | H | H | O | NHCOCH3 |
| H | H | H | H | CH3 | CH2 | NHCOCH3 |
| H | H | H | H | CH3O | CH2 | NHCOCH3 |
| H | H | H | H | CH3 | O | NHCONHCH3 |
| H | H | H | H | CH3O | O | NHCONHCH3 |
| H | H | H | H | Cl | O | NHCONHCH3 |
| H | H | H | H | H | O | NHCONHCH3 |
| H | H | H | H | CH3 | CH2 | NHCONHCH3 |
| H | H | H | H | CH3O | CH2 | NHCONHCH3 |
| H | H | H | H | CH3 | O | NHCH3 |
| H | H | H | H | CH3O | O | NHCH3 |
| H | H | H | H | Cl | O | NHCH3 |
| H | H | H | H | H | O | NHCH3 |
| H | H | H | H | CH3 | CH2 | NHCH3 |
| H | H | H | H | CH3O | CH2 | NHCH3 |
| H | H | H | H | CH3 | O | NCH3CONHCH3 |
| H | H | H | H | CH3O | O | NCH3CONHCH3 |
| H | H | H | H | Cl | O | NCH3CONHCH3 |
| H | H | H | H | H | O | NCH3CONHCH3 |
| H | H | H | H | CH3 | CH2 | NCH3CONHCH3 |
| H | H | H | H | CH3O | CH2 | NCH3CONHCH3 |
| H | H | H | H | CH3 | O | N(C2H5)CO2CH3 |
| H | H | H | H | CH3O | O | N(C2H5)CO2CH3 |
| H | H | H | H | Cl | O | N(C2H5)CO2CH3 |
| H | H | H | H | H | O | N(C2H5)CO2CH3 |

TABLE III-continued

| R | R₁ | R₂ | R₈ | Y' | Q | L |
|---|---|---|---|---|---|---|
| H | H | H | H | CH₃ | CH₂ | N(C₂H₅)CO₂CH₃ |
| H | H | H | H | CH₃O | CH₂ | N(C₂H₅)CO₂CH₃ |
| H | H | H | H | CH₃ | O | NHCO₂Et |
| H | H | H | H | CH₃O | O | NHCO₂Et |
| H | H | H | H | Cl | O | NHCO₂Et |
| H | H | H | H | H | O | NHCO₂Et |
| H | H | H | H | CH₃ | CH₂ | NHCO₂Et |
| H | H | H | H | CH₃O | CH₂ | NHCO₂Et |
| H | H | H | H | CH₃ | O | Cl |
| H | H | H | H | CH₃O | O | Cl |
| H | H | H | H | Cl | O | Cl |
| H | H | H | H | H | O | Cl |
| H | H | H | H | CH₃ | CH₂ | Cl |
| H | H | H | H | CH₃O | CH₂ | Cl |
| H | Cl | H | H | CH₃O | CH₂ | Cl |
| H | CH₃ | H | H | CH₃O | CH₂ | Cl |
| H | CH(CH₃)₂ | H | H | CH₃O | CH₂ | Cl |
| H | H | CH₃ | H | CH₃O | CH₂ | Cl |
| 5-F | H | H | H | CH₃O | CH₂ | Cl |
| 5Cl | H | H | H | CH₃O | CH₂ | Cl |
| 5Br | H | H | H | CH₃O | CH₂ | Cl |
| 5-NO₂ | H | H | H | CH₃O | CH₂ | Cl |
| 5-CF₃ | H | H | H | CH₃O | CH₂ | Cl |
| 5-CH₃ | H | H | H | CH₃O | CH₂ | Cl |
| 5-CH(CH₃)₂ | H | H | H | CH₃O | CH₂ | Cl |
| 5-OCH₃ | H | H | H | CH₃O | CH₂ | Cl |
| 5-OCH(CH₃)₂ | H | H | H | CH₃O | CH₂ | Cl |

| R | R₁ | R₂ | R₈ | Y₁ | Q | L |
|---|---|---|---|---|---|---|
| H | H | H | H | OCH₃ | CH₂ | NCH₃(OCH₃) |
| H | H | H | H | OCH₃ | CH₂ | NHn-C₄H₉ |
| H | H | H | H | OCH₃ | CH₂ | piperidin-1-yl |
| H | H | H | H | OCH₃ | CH₂ | morpholin-4-yl |
| H | H | H | H | OCH₃ | CH₂ | 1-ethylpyrrolidinium |
| H | H | H | H | OCH₃ | CH₂ | NHCOCH₂CH₃ |
| H | H | H | H | OCH₃ | CH₂ | NHCOn-C₄H₉ |
| H | H | H | H | OCH₃ | CH₂ | NHCOCF₃ |
| H | H | H | H | OCH₃ | CH₂ | NHCOCH₂Cl |
| H | H | H | H | OCH₃ | CH₂ | NHCOCCl₃ |

TABLE III-continued

[Structure: R-substituted phenyl with C(R1)(R2)-L group, SO2NHC(O)NR8 linked to pyrimidine with Y' and fused ring containing Q]

| R | R1 | R2 | R8 | Y' | Q | L |
|---|----|----|----|----|---|---|
| H | H | H | H | OCH3 | CH2 | NHC(O)CH2Br |
| H | H | H | H | OCH3 | CH2 | NHC(O)CH=CHCH3 |
| H | H | H | H | OCH3 | CH2 | NHC(O)NHCH2CH3 |
| H | H | H | H | OCH3 | CH2 | NHC(O)NHCH(CH3)2 |
| H | H | H | H | OCH3 | CH2 | NHC(O)NHn-C4H9 |
| H | H | H | H | OCH3 | CH2 | NHC(O)CH(CH3)2 |
| H | H | H | H | OCH3 | CH2 | NHC(O)n-C4H9 |
| H | H | H | H | OCH3 | CH2 | NHC(O)NHCH2CH=CHCH3 |
| H | H | H | H | OCH2CH3 | CH2 | Cl |
| H | H | H | H | OCH2CH3 | O | Cl |
| H | H | H | H | OCH2CH3 | CH2 | Cl |
| H | H | H | H | OCH2CH3 | O | Cl |
| H | H | H | CH3 | CH3 | O | Cl |
| H | H | H | CH3 | CH3 | CH2 | Cl |
| H | H | H | CH3 | OCH3 | O | Cl |
| H | H | H | CH3 | OCH3 | CH2 | Cl |
| H | H | H | OCH3 | OCH3 | CH2 | Cl |
| H | H | H | CH3 | CH3 | O | F |
| H | H | H | CH3 | OCH3 | CH2 | F |
| H | H | H | CH3 | OCH3 | O | F |
| H | F | H | H | OCH3 | O | F |
| H | F | H | H | CH3 | O | F |
| H | F | H | H | OCH3 | CH2 | F |
| H | H | H | H | OCH3 | O | F |
| H | H | H | H | CH3 | O | F |
| H | H | H | H | OCH3 | CH2 | F |

TABLE IV

[Structure: R-substituted phenyl with C(R1)(R2)-L, SO2NHC(O)NR8 linked to pyrimidine with Y' and fused ring containing O]

| R | R1 | R2 | Y' | R8 | L |
|---|----|----|----|----|---|
| H | H | H | CH3 | H | Cl |
| H | H | H | OCH3 | H | Cl |
| H | Cl | H | CH3 | H | Cl |
| H | Cl | H | OCH3 | H | Cl |
| H | H | H | OCH2CH3 | H | Cl |

TABLE IV-continued

| R | R1 | R2 | Y' | R8 | L |
|---|----|----|----|----|---|
| H | Cl | H | OCH2CH3 | H | Cl |

TABLE IV-continued

[Structure: substituted phenyl with C(R1)(R2)L group at ortho, SO2NHC(O)N(R8) linking to pyrimidine with Y' and fused dihydrofuran/oxygen ring; R on phenyl]

| R | R₁ | R₂ | Y' | R₈ | L |
|---|----|----|----|----|---|
| H | H | H | CH₃ | H | pyrrolidin-1-yl |
| H | H | H | OCH₃ | H | pyrrolidin-1-yl |
| H | H | H | OCH₂CH₃ | H | pyrrolidin-1-yl |
| H | H | H | CH₃ | H | N⊕(CH₃)₃ |
| H | H | H | OCH₃ | H | N⊕(CH₃)₃ |
| H | H | H | OCH₂CH₃ | H | N⊕(CH₃)₃ |
| H | H | H | CH₃ | H | NHC(O)CH₃ |
| H | H | H | OCH₃ | H | NHC(O)CH₃ |
| H | H | H | OCH₂CH₃ | H | NHC(O)CH₃ |
| H | H | H | CH₃ | H | NHC(O)NHCH₃ |
| H | H | H | OCH₃ | H | NHC(O)NHCH₃ |
| H | H | H | OCH₂CH₃ | H | NHC(O)NHCH₃ |
| 5-Cl | H | Cl | CH₃ | H | Cl |
| 5-Cl | H | Cl | OCH₃ | H | Cl |
| 5-Cl | H | Cl | OCH₂CH₃ | H | Cl |
| H | H | H | CH₃ | CH₃ | Cl |
| H | H | H | OCH₃ | CH₃ | Cl |
| H | H | H | CH₃ | OCH₃ | Cl |
| H | H | H | OCH₃ | OCH₃ | Cl |
| H | H | H | OCH₃ | H | F |
| H | H | H | CH₃ | H | F |
| H | F | H | OCH₃ | H | F |
| H | F | H | CH₃ | H | F |
| H | H | H | OCH₃ | CH₃ | F |

Exemplary compounds within the structure below that can be made by one or more of the described methods are listed in Table V wherein the substituents R, R₁, R₂, and P are defined as for Formula IV. These lists are not to be considered as limiting, but merely exemplary.

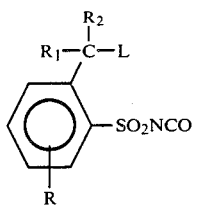

TABLE V

| L | R₁ | R₂ | R |
|---|----|----|---|
| Cl | H | H | H |
| Cl | Cl | H | H |
| Br | H | H | H |
| Br | Cl | H | H |
| Cl | H | CH₃ | H |
| pyrrolidin-1-yl | H | H | H |
| F | H | H | H |
| F | F | H | H |
| N(CH₃)₂ | H | H | H |
| 1-methylpyrrolidinium | H | H | H |
| Cl | H | H | 5-NO₂ |
| Cl | Cl | H | 5-NO₂ |
| Br | H | H | 5-NO₂ |
| Br | Cl | H | 5-NO₂ |
| Cl | H | CH₃ | 5-NO₂ |
| pyrrolidin-1-yl | H | H | 5-NO₂ |
| N(CH₃)₂ | H | H | 5-NO₂ |
| 1-methylpyrrolidinium | H | H | 5-NO₂ |
| Cl | H | H | 5-Cl |
| Cl | Cl | H | 5-Cl |
| Br | H | H | 5-Cl |
| Br | Cl | H | 5-Cl |
| Cl | H | CH₃ | 5-Cl |
| pyrrolidin-1-yl | H | H | 5-Cl |
| N(CH₃)₂ | H | H | 5-Cl |
| 1-methylpyrrolidinium | H | H | 5-Cl |

TABLE VI

Structure: R-phenyl with substituents R₁, R₂, C-L on adjacent position, and SO₂NHC(O)NH- linked to a triazine/pyrimidine ring with two Cl and Z.

| L | R | R₁ | R₂ | Z | m.p. (°C.) |
|---|---|----|----|---|-----------|
| Cl | H | H | H | CH | |
| Cl | H | H | Cl | CH | |
| Br | H | H | H | N | |
| N-pyrrolidinyl | H | H | H | CH | |
| Cl | 5-NO₂ | H | H | CH | |
| Cl | 5-Cl | H | H | CH | |
| Cl | 5-Cl | H | Cl | N | |
| —N(CH₃)C(O)CH₃ | H | H | H | CH | |
| —N(CH₃)C(O)OCH₃ | H | H | H | N | |
| N(CH₃)₂ | H | H | H | CH | |
| Cl | 5-CF₃ | H | H | CH | |
| Cl | 5-OCH₃ | H | H | N | |
| Cl | 5-CH₃ | H | H | CH | |
| morpholino | H | H | H | CH | |
| Cl | H | H | C₂H₅ | N | |
| Cl | H | CH₃ | Cl | CH | |
| F | H | H | H | CH | |
| F | H | F | H | N | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | | | |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 21

Wettable Powder 2-(chloromethyl)-N-[(4,6-dimethylpyrimidin-2-yl)aminocarbonyl]benzenesulfonamide: 80%
   sodium alkylnaphthalenesulfonate: 2%
   sodium ligninsulfonate: 2%
   synthetic amorphous silica: 3%
   kaolinite: 13%

The ingredients are blended, hammer-milled until all the solids are essentially under 50 microns and then reblended.

EXAMPLE 22

Wettable Powder 2-(dichloromethyl)-N-[(4-methoxy-6-methylpyrimidin-2-yl)aminocarbonyl]benzenesulfonamide: 50%
   sodium alkylnaphthalenesulfonate: 2%
   low viscosity methyl cellulose: 2%
   diatomaceous earth: 46%

The ingredients are blended, coarsely hammer-milled and then air-milled to produce particles of active essentially all below 10 microns in diameter. The product is reblended before packaging.

EXAMPLE 23

Granule wettable powder of Example 22: 5%
attapulgite granules (U.S.S. 20–40 mesh; 0.84–0.42 mm): 95%

A slurry of wettable powder containing ≈25% solids is sprayed on the surface of attapulgite granules in a double-cone blender. The granules are dried and packaged.

EXAMPLE 24

Extruded Pellet 2-(chloromethyl)-N-[(4,6-dimethoxy-1,3,5-triazin-2-yl)aminocarbonyl]benzenesulfonamide: 25%
   anhydrous sodium sulfate: 10%
   crude calcium ligninsulfonate: 5%
   sodium alkylnaphthalenesulfonate: 1%
   calcium/magnesium bentonite: 59%

The ingredients are blended, hammer-milled and then moistened with about 12% water. The mixture is extruded as cylinders about 3 mm diameter which are cut to produce pellet about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 25

Oil Suspension 2-(1-chloroethyl)-N-[(4,6-dimethoxy-1,3,5-triazin-2-yl)aminocarbonyl]benzenesulfonamide: 25%
   polyoxyethylene sorbitol hexaoleate: 5%
   highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 26

Wettable Powder 2-(1-chloroethyl)-N-[(4,6-dimethoxy-1,3,5-triazin-2-yl)aminocarbonyl]benzenesulfonamide: 20%
   sodium alkylnaphthalenesulfonate: 4%
   sodium ligninsulfonate: 4%
   low viscosity methyl cellulose: 3%
   attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 27

Aqueous Suspension 2-(dichloromethyl)-N-[(4,6-dimethylpyrimidin-2-yl)aminocarbonyl]benzenesulfonamide: 40%
   polyacrylic acid thickener: 0.3%
   dodecylphenol polyethylene glycol ether: 0.5%
   disodium phosphate: 1%
   monosodium phosphate: 0.5%
   polyvinyl alcohol: 1.0%
   Water: 56.7%

The ingredients are blended and ground together in a sand mill to produce particles essentially all under 5 microns in size.

EXAMPLE 28

Solution 2-(chloromethyl)-N-[(4,6-dimethylpyrimidin-2-yl)amino-carbonyl]benzenesulfonamide, sodium salt: 5%
water: 95%

The salt is added directly to the water with stirring to produce the solution, which may then be packaged for use.

EXAMPLE 29

Low Strength Granule 2-(chloromethyl)-N-[(4,6-dimethoxypyrimidin-2-yl)aminocarbonyl]benzenesulfonamide: 0.1%
attapulgite granules (U.S.S. 20–40 mesh): 99.9%

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 30

Granule 2-(dichloromethyl)-N-[(4-methoxy-6-methylpyrimidin-2-yl)aminocarbonyl]benzenesulfonamide: 80%
   wetting agent: 1%
   crude ligninsulfonate salt (containing 5–20% of the natural sugars): 10%
   attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 31

High Strength Concentrate 2-(dichloromethyl)-N-[(4,6-dimethylpyrimidin-2-yl)aminocarbonyl]benzenesulfonamide: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 32

Wettable Powder 2-(chloromethyl)-N-[(4,6-dimethoxypyrimidin-2-yl)aminocarbonyl]benzenesulfonamide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 33

Wettable Powder 2-(chloromethyl)-N-[(4,6-dimethoxy-1,3,5-triazin-2-yl)aminocarbonyl]benzenesulfonamide: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

UTILITY

The compounds of the present invention are active herbicides. They have utility for broadspectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application, compounds of this invention may be used to modify plant growth beneficially, and also selectively control weeds in crops such as wheat and barley.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.001 to 20 kg/ha with a preferred range of 0.01 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-d) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); $\alpha,\alpha,\alpha$-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',$\epsilon$'-diethyl(methoxymethyl)acetanilide (alachlor); and 1,1-dimethyl-3-($\alpha,\alpha,\alpha$-trifluoro-m-tolyl)urea (fluometuron), and 5-[2-chloro-4-(trifluoromethyl)-phenoxy]-z-nitrobenzoic acid, methyl ester (acifluorfen, methyl).

TEST PROCEDURE A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a nonphytotoxic solvent solution of the compounds of Table IV. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledondary leaves, rice with three leaves, wheat with one leaf, and nutsedge with three-five leaves were sprayed with a nonphytotoxic solvent solution of the compounds of Table A. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The ratings are based on a numberical scale extending from 0 = no injury, to 10 = complete kill. The accompanying descriptive symbols have the following meanings:
G = growth retardation
C = chlorosis/necrosis
E = emergence inhibition
H = formative effects
D = defoliation
6Y = abscised buds or flowers
U = unusual pigmentation.

TABLE A
POST-EMERGENCE

| Structure | kg/ha | BUSH BEAN | COTTON | MORNING-GLORY | COCK-LEBUR | CASSIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| CHCl₂ / SO₂NHCONH-pyrimidine(OCH₃,CH₃) | 0.4 | 9D,8G,6Y | 5U,9D,9G | 10C | 9C | 9C | 2C,9G | 2C,8G | 10C | 9C | 2C,9G | 3U,9C | 5C,9G | | 9C |
| CHCl₂ / SO₂NHCONH-pyrimidine(CH₃,CH₃) | 0.4 | 9C | 9C | 10C | 9C | 9C | 9C | 2C | 9C | 3C,8H | 9C | 9C | 9C | 6C,9G | 10C |
| CH₂Cl / SO₂NHCONH-pyrimidine(OCH₃,OCH₃) | 0.4 | 7C | 3C | 1C | 10C | 1C | 0 | 0 | 0 | 0 | 0 | 2C,3H | 7C | 0 | 2C |
| CH₂Cl / SO₂NHCONH-pyrimidine(OCH₃,OCH₃) | 0.1 | 5C,9G,6Y | 3C,3H,9G | 3C,3H,1C,2H | 2C,9G | 3C,5H | 2C,7G | 1C,3G | 3C,9H | 1C | 1C | 2C,9H | 9C | 1C,8G | 1C,9H |
| CH₂Cl / SO₂NHCONH-pyrimidine(CH₃,CH₃) | 0.1 | 10G,5H | 0 | 10G,7C | 10G | 6G,3C | 3G | 4G | 0 | 0 | 0 | 7G,5H | 10G,9C | 8G,3C | 10C |

TABLE A-continued

| Compound | kg/ha | MORNING-GLORY | COCKLEBUR | CASSIA | NUTSEDGE | CRABGRASS | BARNYARD-GRASS | WILD OATS | WHEAT | CORN | SOYBEAN | RICE | SORGHUM |
|---|---|---|---|---|---|---|---|---|---|---|---|---|---|
| CH₃-CHCl-C₆H₄-SO₂NHCONH-pyrimidine(OCH₃)₂ | 0.4 | 8C | 10C | 9C | 8C | 3G | 3C | 7C | 3G | 0 | 10C | 8C | 7C, 7C |
| CHCl₂-C₆H₄-SO₂NHCONH-pyrimidine(CH₃,OCH₃) | 0.4 | 7C,9G | 9C | 9C | 2C,5G | 7C,9G | 1C,4G | 2C | 0 | 0 | 5U,9C | 9C | 0, 1C,7H |
| (pyrrolidine·HCl)CH₂N-C₆H₄-SO₂NHCONH-pyrimidine(OCH₃)₂ | 0.1 | 3C,8G,6Y | 9C,5G | 6C,9G | 4C,9G | 2C,3G | 3G | 9H | 1C | 0 | 3C,9H | 2C,9G | 9C, 3C,9G |
| (pyrrolidine)CH₂N-C₆H₄-SO₂NHCONH-pyrimidine(OCH₃)₂ | 0.1 | 8D,9G,6Y | 5C,9G | 6C,9G | 4C,9G | 2C,7G | 1C | 2C,9H | 2C | 1C | 3C,9H | 2C,9G | 3C,9G, 2C,9G |

PRE-EMERGENCE

TABLE A-continued

| Structure | | | | | | | | | | | | | |
|---|---|---|---|---|---|---|---|---|---|---|---|---|---|
| CHCl₂–C₆H₄–SO₂NHCONH–pyrimidine(OCH₃, CH₃) | 0.4 | 9G | 9G | 9G | 9G | 8G | 5C,9H | 3C,9G | 9G | 9G | 9H | 10E | 5C,9H |
| CHCl₂–C₆H₄–SO₂NHCONH–pyrimidine(CH₃, CH₃) | 0.4 | 9H | 9H | 4C,9G | 10H | 3C,7G | 3C,9H | 2C,9G | 2C,9G | 9H | 9H | 10E | 10E |
| CH₂Cl–C₆H₄–SO₂NHCONH–pyrimidine(OCH₃, OCH₃) | 0.4 | 3G | 6G,5C | 5G | 0 | 0 | 3G | 0 | 0 | 3C | 2C | 0 | 4G |
| CH₂Cl–C₆H₄–SO₂NHCONH–pyrimidine(OCH₃, CH₃) | 0.1 | 8G | 8H | 8G | 10E | 5G | 2C,8H | 7G | 4G | 8H | 5H | 10E | 1C,9G |
| CH₂Cl–C₆H₄–SO₂NHCONH–pyrimidine(CH₃, CH₃) | 0.1 | 9C | | 6G | | 4G | 5C | 5G | 5G,2C | 6G,3C | 7G,4C | 5G,3H |

TABLE A-continued

| Structure | | | | | | | | | | | | | |
|---|---|---|---|---|---|---|---|---|---|---|---|---|---|
| ![structure with CH3-CHCl, OCH3, OCH3] | 0.4 | 8C | 8C | 5G | 3G | 3C | 8C | 6C | 9C | 9C | 10C | 9C |
| ![structure with CHCl2, OCH3, OCH3] | 0.4 | 9H | 9H | 9G | 9G | 3C | 2C,9H | 6G | 9H | 9H | 1C,9H |
| ![structure with CH2N-pyrrolidine·HCl, OCH3, OCH3] | 0.1 | 9G | 2C | 3C | 3G | 1C | 1C | 0 | 2C,6G | 9H | 9H |
| ![structure with CH2N-pyrrolidine, OCH3, OCH3] | 0.1 | 2C,9G | 2C,5H | 2C,3H | 4G | 1C | 1C,3G | 0 | 2C,6G 3G | 2C,6G 2C,2H | 2C,8G 3C,8H |
| | | | | | | | | | 0 | 3C,8G | 3C,7G | 3C,9G |
| | | | | | | | | | | 2C,7H | 3C,7H | |

Note: Last row represents additional data for fourth structure: 3C,8G 2C,7H 3C,7G 3C,9G

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON FALLSINGTON SILT LOAM

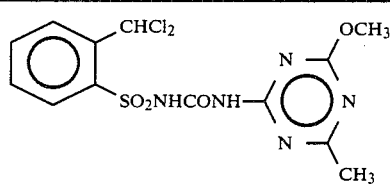

| Rate kg/ha | 0.015 | 0.03 | 0.06 | 0.25 |
|---|---|---|---|---|
| Crabgrass | 0 | 0 | 6G | 8G,6C |
| Barnyardgrass | 0 | 0 | 9G,9C | 10C |
| Sorghum | 5G | 7G,3H | 10C | 10E |
| Wild Oats | 0 | 0 | 7G,5C | 10C |
| Johnsongrass | 0 | 4G,3H | 9G,9C | 10C |
| Dallisgrass | 0 | 2G | 8G,5C | 10C |
| Giant foxtail | 0 | 4G | 10C | 10C |
| Ky. bluegrass | 5G | 6G,3C | 10C | 10C |
| Cheatgrass | 4G | 4G | 10E | 10E |
| Sugarbeets | 0 | 5G | 10C | 10C |
| Corn | 0 | 0 | 10C | 10C |
| Mustard | 9G,8C | 9G,8C | 10C | 10C |
| Cocklebur | 6G,3H | 6G,3H | 8G,5H | 8G,8C |
| Pigweed | — | — | — | — |
| Nutsedge | 0 | 0 | 9G | 10E |
| Cotton | 0 | 2G | 9G | 10C |
| Morningglory | 2G | 5G | 10C | 10C |
| Cassia | 0 | 5G | 10C | 10C |
| Teaweed | 0 | 0 | 10C | 10C |
| Velvetleaf | 0 | 0 | 10C | 10C |
| Jimsonweed | 0 | 0 | 6G | 10C |
| Soybean | 0 | 0 | 9G,9C | 9G,8C |
| Rice | 5G | 6G | 10E | 10E |
| Wheat | 2G | 4G | 8G,8C | 10C |

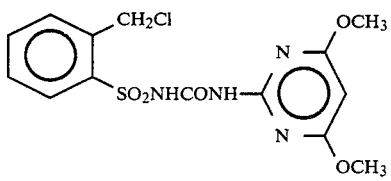

TABLE B-continued
PRE-EMERGENCE ON FALLSINGTON SILT LOAM

| Rate kg/ha | 0.125 | 0.5 |
|---|---|---|
| Crabgrass | 0 | 3G |
| Barnyardgrass | 5G,3C | 7G,3C |
| Sorghum | 8G,5H | 10C |
| Wild Oats | 0 | 0 |
| Johnsongrass | 5G | 7G |
| Dallisgrass | 0 | 3G |
| Giant foxtail | 5G | 10E |
| Ky. bluegrass | 6G,3C | 8G,8C |
| Cheatgrass | 3G | 7G,5C |
| Sugarbeets | 7G,5H | 8G,8C |
| Corn | 8G,5H | 9G,9C |
| Mustard | 10C | 10C |
| Cocklebur | 7G | 9G,8C |
| Pigweed | — | — |
| Nutsedge | 3G | 6G |
| Cotton | 8G | 9G,8C |
| Morningglory | 8G | 9G,8C |
| Cassia | 8G,8C | 8G,8C |
| Teaweed | 10C | 10C |
| Velvetleaf | 8G,9C | 10C |
| Jimsonweed | 0 | 3G |
| Soybean | 8G,5H | 9G,5H |
| Rice | 0 | 6G,4C |
| Wheat | 0 | 0 |

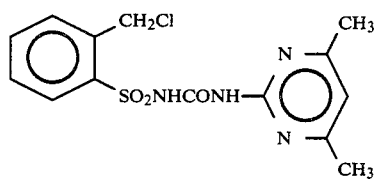

| Rate kg/ha | 0.03 | 0.25 |
|---|---|---|
| Crabgrass | 0 | 0 |
| Barnyardgrass | 0 | 3G |
| Sorghum | 4G | 7G,5H |
| Wild Oats | 0 | 0 |
| Johnsongrass | 0 | 3G |
| Dallisgrass | 0 | 0 |
| Giant foxtail | 0 | 0 |
| Ky. bluegrass | 0 | 0 |
| Cheatgrass | 0 | 5G |
| Sugarbeets | 0 | 2G |
| Corn | 0 | 2C |
| Mustard | 0 | 8G,3C |
| Cocklebur | 0 | 2G |
| Pigweed | 5G | 5G |
| Nutsedge | 0 | 7G |
| Cotton | 0 | 0 |
| Morningglory | 0 | 0 |
| Cassia | 3G | 4G |
| Teaweed | 0 | 2G |
| Velvetleaf | 0 | 6G |
| Jimsonweed | 0 | 0 |
| Soybean | 0 | 0 |
| Rice | 4G | 5G |
| Wheat | 0 | 3G |

| Rate kg/ha | 0.03 | 0.125 |
|---|---|---|
| Crabgrass | 0 | 0 |
| Barnyardgrass | 0 | 4G |
| Sorghum | 4G | 7G,3H |
| Wild Oats | 0 | 0 |
| Johnsongrass | 0 | 7G,3H |
| Dallisgrass | 6G | 10E |
| Giant foxtail | 0 | 0 |
| Ky. bluegrass | 0 | 5G |

TABLE B-continued

PRE-EMERGENCE ON FALLSINGTON SILT LOAM

| | | |
|---|---|---|
| Cheatgrass | 0 | 0 |
| Sugarbeets | 0 | 0 |
| Corn | 0 | 3G |
| Mustard | 4G | 10C |
| Cocklebur | 0 | 0 |
| Pigweed | 0 | 5G |
| Nutsedge | 0 | 0 |
| Cotton | 0 | 0 |
| Morningglory | 0 | 0 |
| Cassia | 0 | 3G |
| Teaweed | 0 | 2G |
| Velvetleaf | 0 | 7G,3H |
| Jimsonweed | 0 | 0 |
| Soybean | 0 | 6G,3H |
| Rice | 0 | 6G,3H |
| Wheat | 0 | 0 |

TEST C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately two weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table C.

TABLE C

[Structure: benzene ring with CHCl₂ and SO₂NHCONH- linked to pyrimidine with OCH₃ and CH₃ substituents]

| Rate kg/ha | 0.06 | 0.25 |
|---|---|---|
| Soybeans | 10G, 6C | 10G, 8C |
| Velvetleaf | 10G, 6C | 10G, 8C |
| Sesbania | 9C | 9C |
| Cassia | 10G, 5C | 10G, 7C |
| Cotton | 9C | 9C |
| Morningglory | 10G, 7C | 10G, 8C |
| Alfalfa | | 9C |
| Jimsonweed | | |
| Cocklebur | 10G, 9C | 10G, 8C |
| Corn | 9G, 3C | 9C |
| Crabgrass | 0 | 3G, 1C |
| Rice | 6G, 1C | 8G, 2C |
| Nutsedge | 6G | 9G |
| Barnyardgrass | 6G, 3C | 8G, 3C |
| Wheat | 3G, 2C | 7G, 2C |
| Giant Foxtail | 4G | 9G |
| Wild Oats | 5G | 7G, 2C |
| Sorghum | 9G, 3C | 10, 7C |

TABLE C-continued

[Structure: benzene ring with CH₂Cl and SO₂NHCONH- linked to pyridine with two OCH₃ substituents]

| Rate kg/ha | 0.03 | 0.125 |
|---|---|---|
| Soybeans | 10G, 6C | 10G, 7C |
| Velvetleaf | 6G | 7G, 3C |
| Sesbania | 10G, 3C | 10G, 9C |
| Cassia | 3G, 1C | 8G, 1C |
| Cotton | 3G, 1C | 4G, 2C |
| Morningglory | 5G | 5G, 1C |
| Alfalfa | 5G, 2C | 7G, 3C |
| Jimsonweed | | |
| Cocklebur | 4G | 3G, 1C |
| Corn | 5G, 5H | 9G, 5C |
| Crabgrass | 2G | 3G, 1C |
| Rice | 5G | 8G, 3C |
| Nutsedge | 4G | 7G, 2C |
| Barnyardgrass | 5G, 1C | 8G, 2C |
| Wheat | 0 | 0 |
| Giant Foxtail | 6G, 1C | 8G, 2C |
| Wild Oats | 0 | 0 |
| Sorghum | 5G, 1C | 7G, 2C |

TEST D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pennsylvanicum*), tumble mustard (*Sisymbrium altissium*) kochia (*Kochia scoparia*), shepherd's purse (*Capsella bursa-pastoris*), Matricaria inodora, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table D.

Several of the compounds tested by this procedure have utility for the pre- and/or post-emergence control of weeds in cereal crops such as wheat and barley.

TABLE D

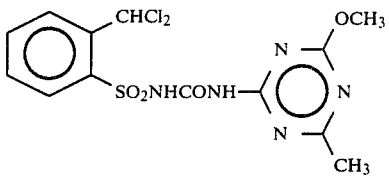

|  | Post-emergence | Pre-emergence | Post-emergence | Pre-emergence | Post-emergence | Pre-emergence | Post-emergence | Pre-emergence |
|---|---|---|---|---|---|---|---|---|
| Rate kg/ha | 0.015 | 0.015 | 0.06 | 0.06 | 0.125 | 0.125 | 0.5 | 0.5 |
| wheat | 0 | 0 | 0 | 0 | 0 | 0 | 0 | 0 |
| barley | 0 | 0 | 0 | 0 | 0 | 0 | 0 | 1G |
| wild oats | 0 | 0 | 0 | 1G | 0 | 0 | 0 | 0 |
| downy brome | 0 | 0 | 1G | 0 | 0 | 2G | 2G | 1G |
| cheatgrass | 0 | 0 | 0 | 1G | 0 | 3G | 2G | 3C,4G |
| blackgrass | 2C | 2G | 7C | 3G | — | 4C,8G | — | 2C,6G |
| annual bluegrass | 0 | 1G | 2C,2G | 3C,7G | 2G | 6G | 6C,5G | 5C,7G |
| green foxtail | 0 | 0 | 10C | 3G | 4C,4G | 2C,6G | 10C | 4C,7G |
| quackgrass | 0 | 0 | 0 | 3G | 0 | 3G | 2G | 7C,7G |
| Italian ryegrass | 0 | 0 | 2G | 5G | 2C,4G | 2G | 4C,6G | 5G |
| ripgut brome | 0 | 0 | 0 | 0 | 0 | 0 | 0 | 2G |
| Russian thistle | 10C | 0 | 10C | 3C,3G | 10C | 4C,5G | 10C | 5C,5G |
| tansy mustard | 10C | 7C,8G | 10C | 8C,8G | 10C | 9C,9G | 10C | 9C,9G |
| smartweed | 9C | — | 10C | — | — | — | — | — |
| jimhill mustard | 10C | 9C,8G | 10C | 9C 9G | 10C | 9C,9G | 10C | 9C,9G |
| Kochia | 7C,8G | 5C,5G | 9C | 7C,8G | 10C | 5G | 10C | 6G |
| shepherd's purse | 10C | 9C,8G | 10C | 10C | 10C | 8C,9G | 10C | 9C,9G |
| false chamomile | 10C | 5C,8G | 10C | 7C,8G | 10C | 9C,9G | 10C | 9C,9G |
| black nightshade | — | — | — | — | — | 5G | — | 4C,6G |
| yellow rocket | 10C | 10C | 10C | 10C | 10C | 9C,9G | 10C | 9C,9G |
| wild mustard | 10C | 7C,7G | 10C | 9C,8G | 10C | 7C,8G | 10C | 9C,9G |
| wild buckwheat | 6C,5G | 1C,1G | 8C,7G | 2C,3G | 10C | 2C,2G | 10C | 5C,6G |

TEST E

Test samples were formulated and applied directly to the water of paddies three days after transplanting of Japonica rice. The paddies were maintained in a greenhouse, and plant response ratings were taken one and three weeks after application.

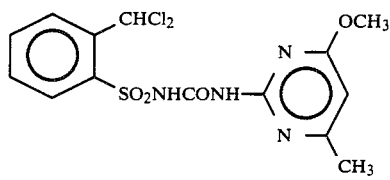

| Treatment | Rice 1 Week | Rice 3 Weeks | Barn-yard-* grass 3 Weeks | Water* Chestnut 3 Weeks | Scirpus* 3 Weeks |
|---|---|---|---|---|---|
| 5 g/ha | 0 | 0 | 5G | 8G | 0 |
| 20 g/ha | 0 | 5G | 8G | 9G | 5G |

*Echinochloa sp., Eleocharis sp., and Scirpus sp., respectively.

TEST F

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in a non-phytotoxic diluent and sprayed at 560 l/ha in four methods of application: soil surface, tuber/soil, soil incorporated and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table F based on the same rating system as described in procedure A.

TEST F
NUTSEDGE

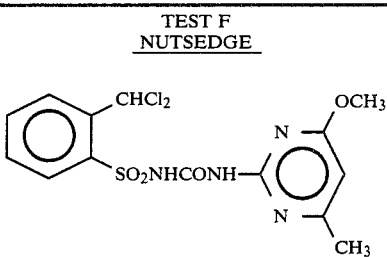

| | Response Rating (after 4 weeks) | | | |
|---|---|---|---|---|
| Rate kg/ha | Preemerg. Soil Surface | Tuber Spray | Soil Incorp. | Postemerg. |
| 0.01 | 3G | 6G | 7G | 0 |
| 0.03 | 7G | 7G | 8G | 0 |
| 0.125 | 9G | 9G | 9G | 4C,7G |

What is claimed is:

1. A compound selected from

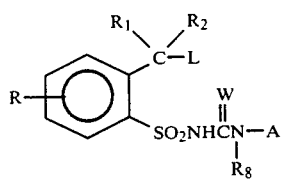

wherein

L is Cl, F, Br, $NR_3R_4$, $N^+R_3R_4R_4'$, $N(R_4)C(O)R_5$, $N(R_4)C(O)NHR_6$ or $N(R_4)C(O)OR_7$;

R is H, F, Cl, Br, $NO_2$, $CF_3$, $C_1-C_3$ alkyl or $C_1-C_3$ alkoxy;

$R_1$ is H, F, Cl or $C_1-C_4$ alkyl;

$R_2$ is H or $CH_3$;

$R_3$ is H, $C_1-C_4$ alkyl or $OCH_3$;

$R_4$ is H or $C_1-C_4$ alkyl;

$R_3$ and $R_4$ can be taken together to form $-(CH_2)_4-$, $-(CH_2)_5-$ or $-(CH_2)_2O(CH_2)_2-$;

$R_4'$ is H, $CH_3$ or $CH_2CH_3$;

$R_5$ is $C_1-C_4$ alkyl optionally substituted with 1-3 atoms of F, Cl or Br, or $C_3-C_4$ alkenyl;

$R_6$ is H, $C_1-C_4$ alkyl or $C_3-C_4$ alkenyl;

$R_7$ is $C_1-C_4$ alkyl;

$R_8$ is H, $CH_3$ or $OCH_3$;

A is

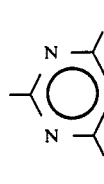

W is O or S;
$Y^1$ is H, $CH_3$, $OCH_3$ or $OCH_2CH_3$; and
Q is O;
and their agriculturally suitable salts; provided that:
 (1) when $R_1$ is Cl, then L is Cl or Br and $R_2$ is H;
 (2) when $R_3$ is $OCH_3$, then $R_4$ is $CH_3$;
 (3) when W is S, then $R_8$ is H; and
 (4) when L is F, then $R_1$ is H, F, or $C_1-C_4$ alkyl.

2. A compound of claim 1 wherein W is O and $R_8$ is H or $CH_3$.

3. A composition suitable for controlling the growth of undesired vegetation which comprises an effective amount of a compound of claim 1 and at least one of the following: surfactant, solid or liquid diluent.

4. A method for controlling the growth of undesired vegetation which comprises applying to the locus to be protected an effective amount of a compound of claim 1.

5. The compound of claim 1, 2-(dichloromethyl)-N-[(5,6-dihydro-4-methylfuro[2,3-d]pyrimidin-2-yl)aminocarbonyl]benzenesulfonamide 6. A composition suitable for controlling the growth of undesired vegetation which comprises an effective amount of the compound of claim 5 and at least one of the following: surfactant, solid or liquid diluent.

7. A method for controlling the growth of undesired vegetation which comprises applying to the locus to be protected an effective amount of the compound of claim 5.

* * * * *